US009458102B2

(12) United States Patent
Karpen et al.

(10) Patent No.: US 9,458,102 B2
(45) Date of Patent: Oct. 4, 2016

(54) DERIVATIVES OF TETRACAINE

(71) Applicants: OREGON HEALTH & SCEINCE UNIVERSITY, Portland, OR (US); WILLAMETTE UNIVERSITY, Salem, OR (US)

(72) Inventors: Jeffrey Karpen, Elk Grove, CA (US); Sarah Kirk, Salem, OR (US); Adriana Andrade, Portland, OR (US); Michelle Schaffer, Frederick, MD (US); Kenneth Melich, Wilsonville, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 0 days.

(21) Appl. No.: 13/715,334

(22) Filed: Dec. 14, 2012

(65) Prior Publication Data

US 2014/0018422 A1 Jan. 16, 2014

Related U.S. Application Data

(60) Provisional application No. 61/576,777, filed on Dec. 16, 2011.

(51) Int. Cl.

| | |
|---|---|
| ***A61K 31/01*** | (2006.01) |
| ***A61K 31/075*** | (2006.01) |
| ***A61K 31/095*** | (2006.01) |
| ***A61K 31/13*** | (2006.01) |
| ***A61K 31/16*** | (2006.01) |
| ***A61K 31/21*** | (2006.01) |
| ***C07C 327/48*** | (2006.01) |
| ***C07C 237/34*** | (2006.01) |
| ***C07C 229/60*** | (2006.01) |
| ***C07C 229/64*** | (2006.01) |
| ***C07C 255/58*** | (2006.01) |

(52) U.S. Cl.

CPC ............ *C07C 327/48* (2013.01); *A61K 31/01* (2013.01); *A61K 31/075* (2013.01); *A61K 31/095* (2013.01); *A61K 31/13* (2013.01); *A61K 31/16* (2013.01); *A61K 31/21* (2013.01); *C07C 229/60* (2013.01); *C07C 229/64* (2013.01); *C07C 237/34* (2013.01); *C07C 255/58* (2013.01)

(58) Field of Classification Search

CPC .. A61K 31/01; A61K 31/075; A61K 31/095; A61K 31/13; A61K 31/16; A61K 31/21

USPC ........................................................ 514/522

See application file for complete search history.

(56) References Cited

U.S. PATENT DOCUMENTS 2,073,100 A * 3/1937 Eisleb .......................... 546/233

OTHER PUBLICATIONS

Andrade et al. ("Cyclic Nucleotide-Gated Channel Block by Hydrolysis-Resistant Tetracaine Derivatives" Journal of Medicinal Chemistry, 2011, 54, 4904-4912).*

H. Amiel et al., "Tetracaine Hydrochloride 0.5% Versus Lidocaine 2% Jelly as a Topical Anesthetic Agent in Cataract Surgery", Journal of Cataract Refraction Surgery, vol. 33, Jan. 2007, pp. 98-100.

A. Fodor et al., "Mechanism of Tetracaine Block of Cyclic Nucleotide-gated Channels", The Journal of General Physiology, vol. 109, Jan. 1, 1997, pp. 3-14.

B. Hille, "Local Anesthetics: Hydrophilic and Hydrophobic Pathways for the Drug-Receptor Reaction", The Journal of General Physiology, vol. 69, 1977, pp. 497-515.

W. Kalow, "Hyrdrolysis of Local Anesthetics by Human Serum Cholinesterase", Laboratory of Pharmacology, University of Pennsylvania, Philadelphia, Pennsylvania, published Sep. 19, 1951, pp. 122-134.

F. N. Quandt et al., "Voltage-Dependent Gating and Block of the Cyclic-GMP-Dependent Current in Bovine Rod Outer Segements", Neuroscience, vol. 42, No. 3, 1991, pp. 629-638.

P. P. M. Schnetkamp, "Cation Selectivity of and Cation Binding to the cGMP-Dependent Channel in Bovine Rod Outer Segment Membranes", The Journal of General Physiology, vol. 96, Sep. 1990, pp. 517-534.

T. Strassmaier et al., "Block of Cyclic Nucleotide-Gated Channels by Tetracaine Derivatives: Role of Apolar Interactions at Two Distinct Locations", Department of Physiology and Pharmacology, Oregon Health & Science University, Bioorganic & Medicinal Chemistry Letters 18, 2008, pp. 645-649.

* cited by examiner

*Primary Examiner* — Yong Chong

(74) *Attorney, Agent, or Firm* — Jeffrey M. Jackson

(57) ABSTRACT

Disclosed herein are derivatives of tetracaine that, among other things, block cyclic nucleotide gated (CNG) channels and are useful in the treatment of diseases characterized by overactive CNG channels such as retinal degeneration diseases.

8 Claims, 7 Drawing Sheets

DERIVATIVES OF TETRACAINE

PRIORITY CLAIM

This application claims priority to U.S. Provisional Application 61/576,777, filed 16 Dec. 2011, which is hereby incorporated by reference in its entirety.

ACKNOWLEDGEMENT OF GOVERNMENT SUPPORT

This invention was made with the support of the United States government under grant numbers R01 EY009275 and R01 MH071625, both of which were awarded by the National Institutes of Health.

FIELD

Generally, the field relates to small molecule compounds for use in pharmaceutical compositions. More specifically, the field relates to derivatives of tetracaine.

BACKGROUND

Cyclic nucleotide-gated (CNG) ion channels are known for their role in phototransduction in retinal photoreceptors and in odorant transduction in the olfactory epithelium (Fesenko E E et al, *Nature* 313, 310-313 (1985) and Nakamura T & Gold G H, *Nature* 325, 442-444 (1987) both of which are incorporated by reference herein.) CNG channels are also present in other brain regions and nonsensory tissues, but their physiological roles are much less clear (Kuzmiski J B & MacVicar B A, *J Neurosci* 21, 8707-8714 (2001); Parent A et al, *J Neurophysiol* 79, 3295-3301 (1998); Kaupp U B & Seifert R et al, *Physiol Rev* 82, 769-824 (2002); Matulef K & Zagotta W N, *Annu Rev Cell Dev Biol* 19, 23-44 (2003); and Biel M & Michalakis S, *Handb Exp Pharmacol* 191, 111-136 (2009), all of which are incorporated by reference herein.)

CNG channel activation in photoreceptors is regulated by the cytoplasmic concentration of cGMP, which binds to and opens the channel to allow influx of $Na^+$ and $Ca^{2+}$ ions. Alterations of CNG channel activity have been observed in some forms of retinitis pigmentosa, a group of inherited diseases that cause progressive degeneration of rod and cone photoreceptors (Farber D B & Lolley R N, *J Neurochem* 28, 1089-1095 (1977); Bowes C et al, *Nature* 347, 677-680 (1990); Pierce E A, *BioEssays* 23, 605-618 (2001); Pacione L R et al, *Annu Rev Neurosci* 26, 657-700 (2003); Olshevskaya E V et al, *J Neurosci* 24, 6078-6085 (2004); Nishiguchi K M et al, *Invest Opthalmol Visual Sci* 45, 3863-3870 (2004); Trifunovic D et al, *J Comp Neurol* 518, 3604-3617 (2010), all of which are incorporated by reference herein.) Mutations that cause elevated cGMP levels lead to prolonged channel activation and $Ca^{2+}$-triggered cell death (Pierce, 2001 supra; Trifunovic, 2010 supra; He L et al, *J Biol Chem* 275, 12175-12184 (2000); Rohrer B et al, *J Biol Chem* 279, 41903-41910 (2004); and Doonan F et al, *Invest Ophthalmol Visual Sci* 46, 3530-3538 (2005); all of which are incorporated by reference herein. In mouse models, reduction of CNG channel activity strongly correlated with improvements in the overall progression of the disease (Fox D A et al, *Eur J Ophtalmol* 13, S44-S56 (2003); Paquet-Durand F et al, *Hum Mol Genet* 20, 941-947 (2011); Vallazza-Deschamps G et al, *Eur J Neurosci* 22, 1013-1022 (2005); Woodruff M L et al, *J Neurosci* 27, 8805-8815 (2007); and Liu X et al, *PLoS One* 4, e8438 (2009) all of which are incorporated by reference herein.)

The most widely used CNG channel antagonist in research, I-cis-diltiazem, is an incomplete blocker (Stern J H et al, *Proc Natl Acad Sci USA* 83, 1163-1167 (1986); Hashimoto Y et al, *Eur J Pharmacol* 391, 217-233 (2000); Haynes L W, *J Gen Physiol* 100, 783-801 (1992); Galizzi J P et al, *J Biol Chem* 261, 1393-1397 (1986) all of which are incorporated by reference herein). CNG channels are also blocked by some local anesthetics, one example being tetracaine [2-(dimethylamino)ethyl 4-(butylamino)benzoate], which is referred to herein as compound 1 (Quandt F N et al, *Neuroscience* 42, 629-638 (1991); Schnetkamp P P, *Biochemistry* 26, 3249-3253 (1987); Schnetkamp P P, *J Gen Physiol* 96, 517-534 (1990), all of which are incorporated by reference herein.) Compound 1 blocks CNG channels with relatively high affinity, although differently from voltage-gated sodium channels. Similarly to sodium channels, the interaction of compound 1 with CNG channels is thought to be located in the selectivity filter and the pore region (Sunami A et al, *Proc Natl Acad Sci USA* 94, 14126-14131 (1997); Ragsdale D S et al, *Science* 265, 1724-1728 (1994); Ragsdale D S et al, *Proc Natl Acad Sci USA* 93, 9270-9275 (1996); Catterall W A, *Novartis Found Symp* 241, 206-218 (2002); Fodor A A et al, *J Gen Physiol* 110, 591-600 (1997), all of which are incorporated by reference herein).

The CNG channels of retinal photoreceptors are non-selective cation conductances that regulate the membrane potential in response to light (Fesenko E E, et al, *Nature* 313, 310 (1985) and Nakamura T & Gold G H, *Nature* 325, 442 (1987), both of which are incorporated by reference herein.) Unlike voltage-gated potassium channels, these channels are directly activated by the binding of cGMP, and are minimally regulated by voltage. In photoreceptors, photons trigger a signaling cascade that leads to a decrease in cGMP levels and closure of channels.

SUMMARY

Compound 1 binds to sodium channels with high affinity when the sodium channel is in its open, inactivated-state (Hille B, *J Gen Physiol* 69, 497-515 (1977), incorporated by reference herein). Compound 1 also binds to CNG channels, with high affinity to the inactive, closed state (Fodor A A et al *J Gen Physiol* 109, 3-14 (1997) incorporated by reference herein.)

Disclosed herein are amide and thioamide linkage derivatives of compound 1, and a previously described compound 1 derivative called compound 5 (Strassmeier T et al, *Bioorg Med Chem Lett* 18, 645-649 (2008), incorporated by reference herein.)

Compound 1 is clinically approved for temporary anesthesia in various surgical procedures, including those involving the eye (Fichman R A, *J Cataract Refractive Surg* 22, 612-614 (1996) and Amiel H & Koch P S *J Cataract Refractive Surg* 33, 98-100 (2007), both of which are incorporated by reference herein.)

The effects of compound 1 are localized and short-lived because of its rapid degradation by esterases (Kalow W, *J Pharmacol Exp Ther* 104, 122-134 (1952), incorporated by reference herein). Therefore, a major challenge in developing a CNG channel blocker based upon compound 1 is that compound 1 is subject to hydrolysis and therefore biologically unstable. Compounds that block CNG channels that are more resistant to hydrolysis than compound 1 would be important products for use in the treatment of retinal degeneration and as anesthetics because they would be more stable than compound 1 or compound 5.

The compounds newly disclosed herein bind CNG with high affinity in the closed state and are more resistant to hydrolysis by serum cholinesterase (butyrylcholinesterase) and other proteases. Butyrylcholinesterase is the most abundant serum cholinesterase present in the eye and therefore the disclosed compounds will be particularly effective in the eye.

Further, tetracaine (compound 1) is well known to have local anesthetic properties. Therefore, the disclosed compounds are likely to also have local anesthetic properties. Based upon their resistance to hydrolysis and ability to bind CNG channels with higher affinity than tetracaine, the disclosed compounds likely will have value as long lasting local anesthetics.

The disclosed compounds have the structure:

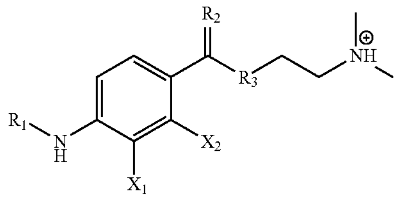

wherein $R_1$ is alkyl, $R_2$ is O or S, $R_3$ is NH or O, $X_1$ is H, nitro, methoxy, methyl, cyano, or halo; and $X_2$ is H, nitro, methoxy, methyl, cyano, or halo, provided that $X_1$ and $X_2$ are not both H when $R_3$ is O.

In further examples, the compounds have the structure:

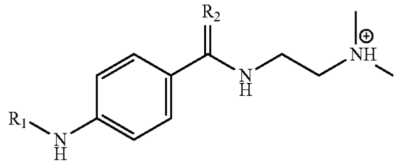

wherein $R_1$ is alkyl and $R_2$ is S or O. In further examples of the compound, $R_1$ is butyl or octyl. In still further examples, $R_1$ is butyl and $R_2$ is O, $R_1$ is octyl and $R_2$ is O, $R_1$ is butyl and $R_2$ is S, or $R_1$ is octyl and $R_2$ is S.

Additional examples of the compounds have the structure:

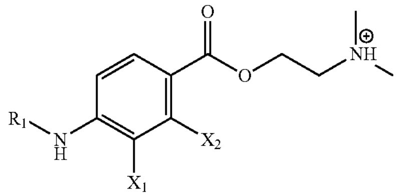

wherein $R_1$ is alkyl, $X_1$ is H, nitro, methoxy, methyl, cyano, or halo; and wherein $X_2$ is H, nitro, methoxy, methyl, cyano, or halo; provided that $X_1$ and $X_2$ are not both H.

Still more examples of the compounds have the structure:

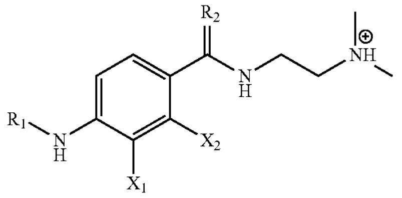

wherein $R_1$ is alkyl, $R_2$ is S or O and wherein $X_1$ is H or halo; and wherein $X_2$ is H or halo. In still further examples, $R_1$ is octyl.

The disclosed compounds may be used in the formulation of pharmaceutical compositions. Pharmaceutical compositions that include the disclosed compounds may be used to block CNG channels in vitro and in vivo, to treat diseases caused by overactivity of CNG channels such as retinal diseases and to be used as local anesthetics.

DETAILED DESCRIPTION

Figure 1:
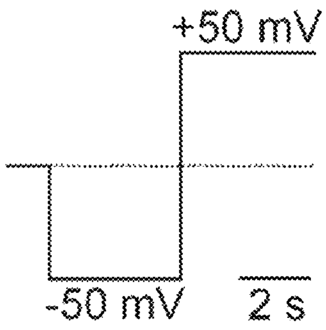
FIG. 1 is a graph showing the voltage step protocol used to test blocking of CNG by compounds. Time scale is shown in the lower left-hand corner of the panel and inset and the zero current level is indicated by the dotted line.

Disclosed herein are compounds that may be used in pharmaceutical compositions. In some examples of the compounds, the compounds have the structure:

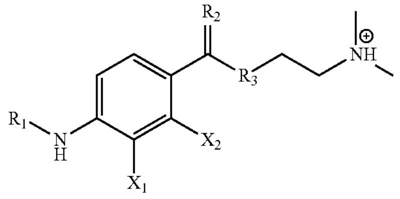

wherein $R_1$ is alkyl, $R_2$ is O or S, $R_3$ is NH or O, $X_1$ is H, nitro, methoxy, methyl, cyano, or halo, $X_2$ is H, nitro, methoxy, methyl, cyano, or halo, provided that $X_1$ and $X_2$ are not both H when $R_3$ is O.

In further examples, the compounds have the structure:

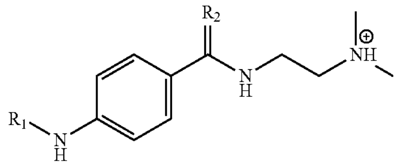

wherein $R_1$ is alkyl and $R_2$ is S or O.

In further examples of compounds of this structure, $R_1$ is butyl or octyl, such as in the following compounds:

Compound 6

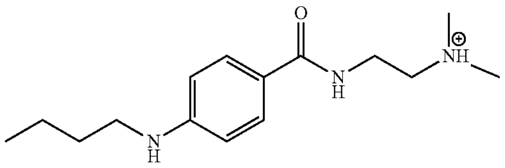

-continued

Compound 7

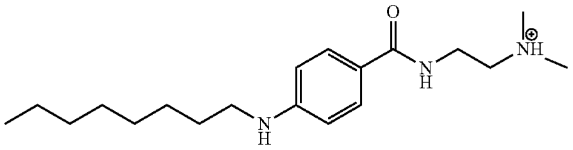

Compound 8

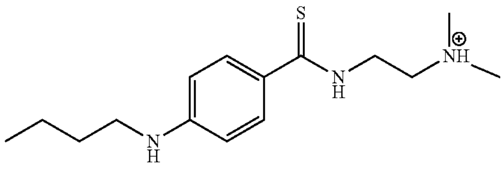

Compound 9

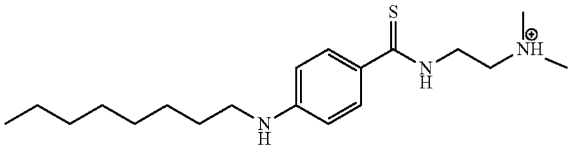

In other examples, the compounds have the structure:

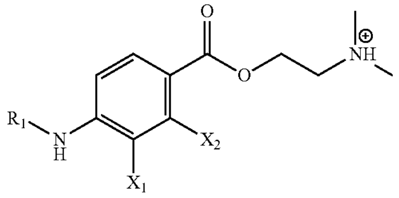

wherein $R_1$ is alkyl, $X_1$ is H, nitro, methoxy, methyl, cyano, or halo and wherein $X_2$ is H or halo provided that $X_1$ and $X_2$ are not both H.

In further examples, R1 is butyl or octyl as in the following:

Compound 12a

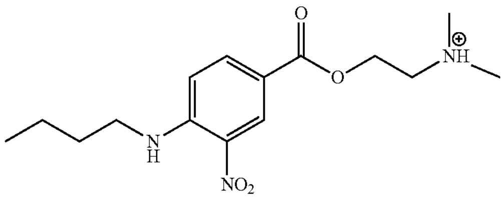

Compound 12b

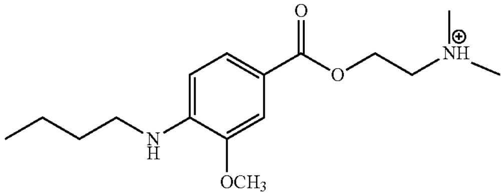

-continued

Compound 12c

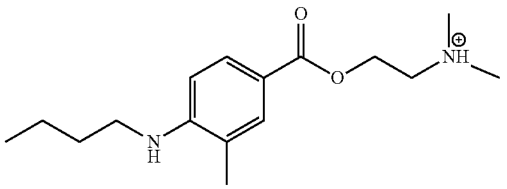

Compound 12d

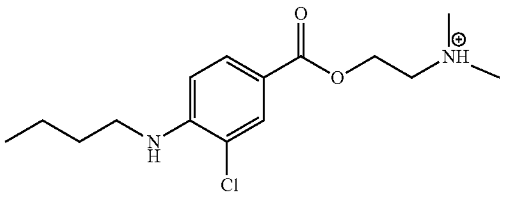

Compound 14a

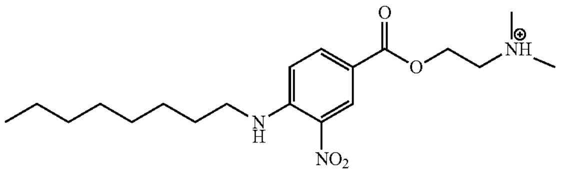

Compound 14b

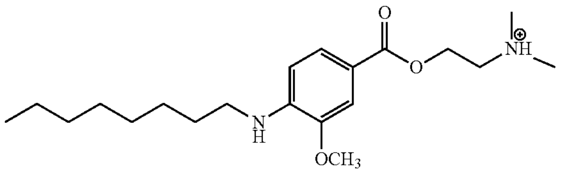

Compound 14c

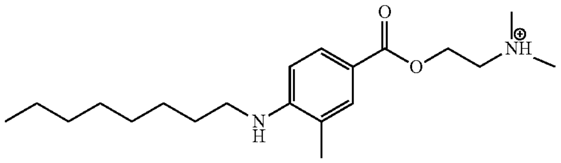

Compound 14d

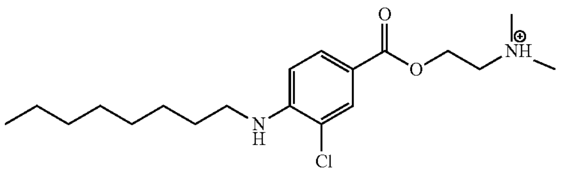

Compound 14e

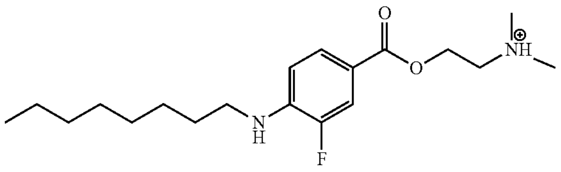

Compound 14f

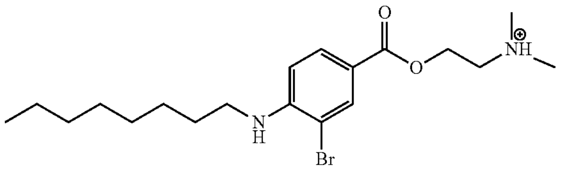

-continued

Compound 14g

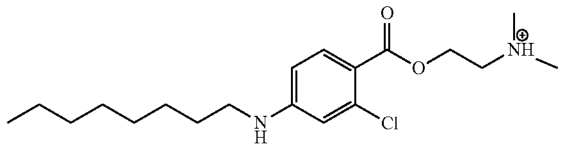

Compound 14h

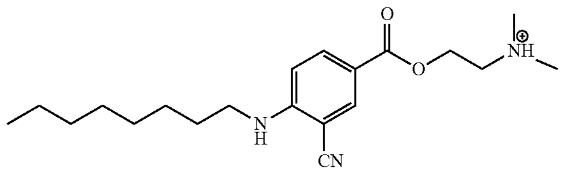

Still further examples of the compound include a compound with the structure:

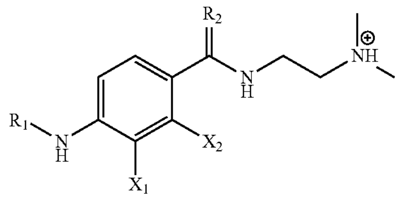

wherein $R_1$ is alkyl, $R_2$ is O or S, $X_1$ is H or halo, and $X_2$ is H or halo.

In further examples, $R_1$ is octyl as in the following:

Compound 15

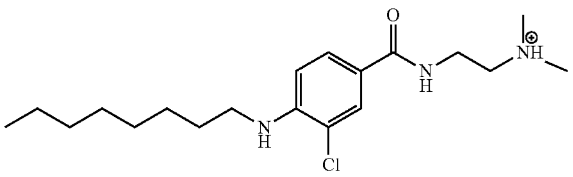

Compound 16

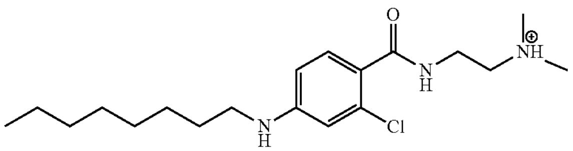

Compound 17

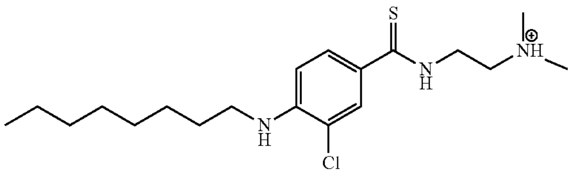

Compound 18

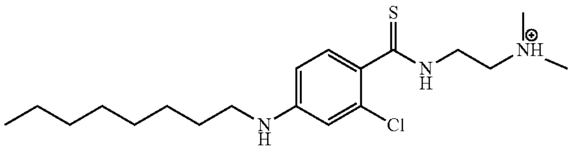

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Variables such as $R_1$, $R_2$, $R_3$, $X_1$, $X_2$, $X_3$ used throughout the disclosure are the same variables as previously defined unless stated to the contrary.

"Administration of" and "administering a" compound refers to providing a compound or a pharmaceutical composition comprising a compound as described herein. The compound or composition can be administered by another person to the subject or it can be self-administered by the subject.

The term "alkyl" refers to a branched or unbranched saturated hydrocarbon group, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Alkyl groups may be "substituted alkyls" wherein one or more hydrogen atoms are substituted with a substituent such as halogen, cycloalkyl, alkoxy, amino, hydroxyl, aryl, or carboxyl.

The term "anesthetic" refers to an agent that produces a reversible loss of sensation in an area of a subject's body such as a tissue, limb, organ or other part of the body. As used herein, the term anesthetic also encompasses an analgesic, which is an agent that lessens, alleviates, reduces, relieves or extinguishes pain in an area of a subject's body. An anesthetic may be administered locally, in which sensation is lost in one or more discrete parts of the body or generally in which sensation is lost in effectively all of the body.

"Derivative" refers to a compound or portion of a compound that is derived from or is theoretically derivable from a parent compound.

Treating refers to inhibiting the full development of a disease or condition, for example, in a subject who is at risk for a disease that involves retinal degeneration. "Treatment" refers to a therapeutic intervention that ameliorates a sign or symptom of a disease or pathological condition after it has begun to develop. As used herein, the term "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. Treating also refers to any quantitative or qualitative reduction of the signs or symptoms of the disease including prevention of retinal degeneration, or complete cure of retinal degeneration, relative to a control such as a standard therapy or an untreated control. A "prophylactic" treatment is a treatment administered to a subject who does not exhibit signs of a disease or exhibits only early signs for the purpose of decreasing the risk of developing pathology. "Coadminister" is meant that each of at least two compounds are administered during a time frame wherein the respective periods of biological activity overlap. Thus, the term includes sequential as well as coextensive administration of two or more drug compounds.

The terms "pharmaceutically acceptable salt" or "pharmacologically acceptable salt" refers to salts prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., J. Pharm. Sci. 66:1 (1977).

The term "subject" includes human subjects, veterinary subjects, and laboratory animal test subjects.

An "effective amount" or "therapeutically effective amount" refers to a quantity of a specified agent sufficient to achieve a desired effect in a subject being treated with that agent. For example, this may be the amount of a compound disclosed herein useful in detecting or treating thyroid cancer in a subject. Ideally, a therapeutically effective amount of an agent is an amount sufficient to inhibit or treat the disease without causing a substantial cytotoxic effect in the subject. The therapeutically effective amount of an agent will be dependent on the subject being treated, the severity of the affliction, and the manner of administration of the therapeutic composition. Methods of determining a therapeutically effective amount of the disclosed compound sufficient to achieve a desired effect in a subject in need of local anesthesia and/or suffering from a disease caused by overactivity of CNG channels such as retinal disease are known to those of skill in the art.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). The term "prodrug" also is intended to include any covalently bonded carriers that release an active parent drug of the present invention in vivo when the prodrug is administered to a subject. Since prodrugs often have enhanced properties relative to the active agent such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts Protective Groups in Organic Synthesis; 5 3rd Ed.; John Wiley & Sons, New York, 1999. In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxyl functions amino is trityl. Other conventional protecting groups are known and suitable protecting groups can be selected by those of skill in the art in consultation with Greene and Wuts Protective Groups in Organic Synthesis; 3rd Ed.; John Wiley & Sons, New York, 1999.

When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

The compounds disclosed herein may be included in pharmaceutical compositions (including therapeutic and prophylactic formulations), typically combined together with one or more pharmaceutically acceptable vehicles or carriers and, optionally, other therapeutic ingredients (for example, antibiotics and anti-inflammatories). The compositions disclosed herein may be advantageously combined and/or used in combination with other anesthetic agents such as general anesthetics or with other treatments for retinal diseases.

Such pharmaceutical compositions can be administered to subjects by a variety of mucosal administration modes, including by oral, rectal, intranasal, intrapulmonary, intravitrial, or transdermal delivery, or by topical delivery to other surfaces including the eye. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Mont.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl(meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres, and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanoparticles prepared from a suitable polymer, for example, 5 isobutyl 2-cyanoacrylate (see, for example, Michael et al., J. Pharmacy Pharmacol. 43:1-5, 1991), and dispersed in a biocompatible dispersing medium, which yields sustained delivery and biological activity over a protracted time. Alternatively, the compound may be combined with a mesoporous silica nanoparticle including a mesoporous silica nanoparticle complex with one or more polymers conjugated to its outer surface.

The pharmaceutical compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like. Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-coglycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, Sustained and Controlled Release Drug Delivery Systems, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675, 189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

Typical subjects intended for treatment with the compositions and methods of the present disclosure include humans, as well as non-human primates and other animals such as companion animals, livestock animals, animals used in models of retinitis pigmentosa, or animals used in pharmaceutical testing, such as pharmacokinetics and toxicological testing, including mice, rats, rabbits, and guinea pigs.

To identify subjects for prophylaxis or treatment according to the methods of the disclosure, accepted screening methods are employed to determine risk factors associated with a parasitic infection to determine the status of an existing disease or condition in a subject.

The administration of the disclosed compounds and pharmaceutical compositions can be for prophylactic or therapeutic purposes. When provided prophylactically, the compound is provided in advance of any symptom. The prophylactic administration of the compound serves to prevent or ameliorate any subsequent disease process. When provided therapeutically, the compound is provided at or after the onset of a symptom of disease or infection. An anesthetic administered prophylactically may be administered prior to an event expected to cause pain (such as surgery.) Alternatively, an anesthetic administered therapeutically may be administered after an event causing pain (such as an injury) in order to provide palliative care.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 100 mg/kg body weight, such as about 0.05 mg/kg to about 50 mg/kg body weight, or about 0.5 mg/kg to about 5 mg/kg body weight.

Dosage can be varied to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The instant disclosure also includes kits, packages and multi-container units containing the herein described pharmaceutical compositions, active ingredients, and/or devices and consumables that facilitate the administration the same for use in the prevention and treatment of diseases and other conditions in mammalian subjects. In one example, this component is formulated in a pharmaceutical preparation for delivery to a subject. The conjugate is optionally contained in a bulk dispensing container or unit or multiunit dosage form. Optional dispensing devices can be provided, for example a pulmonary or intranasal spray applicator. Packaging materials optionally include a label or instruction indicating for what treatment purposes and/or in what manner the pharmaceutical agent packaged therewith can be used.

The compounds may be used in the treatment of diseases that are caused by improper function of CNG channels. CNG channels are central participants in the pathology of certain forms of retinal degeneration including some forms of retinitis pigmentosa. For example, mutations that result in increased cGMP levels, such as mutations in the cGMP phosphodiesterase or the guanylyl cyclase activating protein 1 of retinal rods, can cause a massive influx of sodium and calcium through CNG channels. Gain-of-function CNG channel mutations can have similar effects. Gain-of-function CNG mutations can cause apoptosis, metabolic overload, and retinal degeneration. CNG channel blockers are would be effective treatments for these blinding diseases. Such blockers may be administered through intravitreal injection, subretinal injection and/or topically.

The compounds may be used as local anesthetics. There are situations in which longer lasting anesthetics are desirable, particularly anesthetics resistant to hydrolysis. Several attempts have been made to achieve longer-lasting local anesthetics (Mannheimer W et al, J Am Med Assoc 154, 29-32 (1954): Epstein-Barash H Et al, Proc Natl Acad Sci USA 106, 7125-7130 (2009); and Ivani G et al, Minerva Anestesiol 67, 20-23 (2001), all of which are incorporated by reference herein. Indeed, there have been some attempts to increase the half-life of compound 1 in biological preparations (Boedeker B H et al, J Clin Pharmacol 34, 699-702 (1994); Fisher R et al, Br J Anaesth 81, 972-973 (1998); Wang G K et al, Anesthesiology 88, 417-428 (1998); all of which are incorporated by reference herein).

EXAMPLES

The following examples are illustrative of disclosed methods. In light of this disclosure, those of skill in the art will recognize that variations of these examples and other examples of the disclosed method would be possible without undue experimentation.

Examples 1-6 pertain to compounds having the structure:

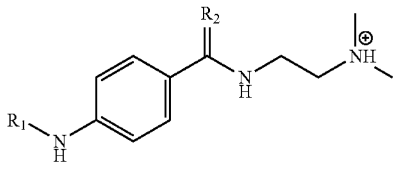

wherein $R_1$ is alkyl and $R_2$ is S or O. In further examples of compounds of this structure, $R_1$ may be butyl or octyl.

Example 1

Synthesis of Compounds

Compound 1 derivatives were prepared according to Scheme 1. An alkyl substituent was added to the amino end of 4-aminobenzoic acid (2) via reductive amination using a synthesis adapted from Sato S et al, *Tetrahedron* 60, 7899-7906 (2004), incorporated by reference herein. The resulting alkylated benzoic acid derivatives (3 and 4) were then activated at the carboxylic acid with 1, 10-carbonyldiimidazole (CDI) and subsequently esterified or amidated using 2-(dimethylamino)ethanol or N',N'-dimethylethane-1,2-diamine, respectively, to yield target compounds 5, 6, and 7 (Staab H A, *Agnew Chem, Int Ed Engl* 1, 351-367 (1962), incorporated by reference herein.) Compounds 6 and 7 were further treated with Lawesson's reagent to yield target thioamide compounds 8 and 9 (Ozturk T et al, *Chem Rev* 107, 5210-5278 (2007) incorporated by reference herein).

Scheme 1:

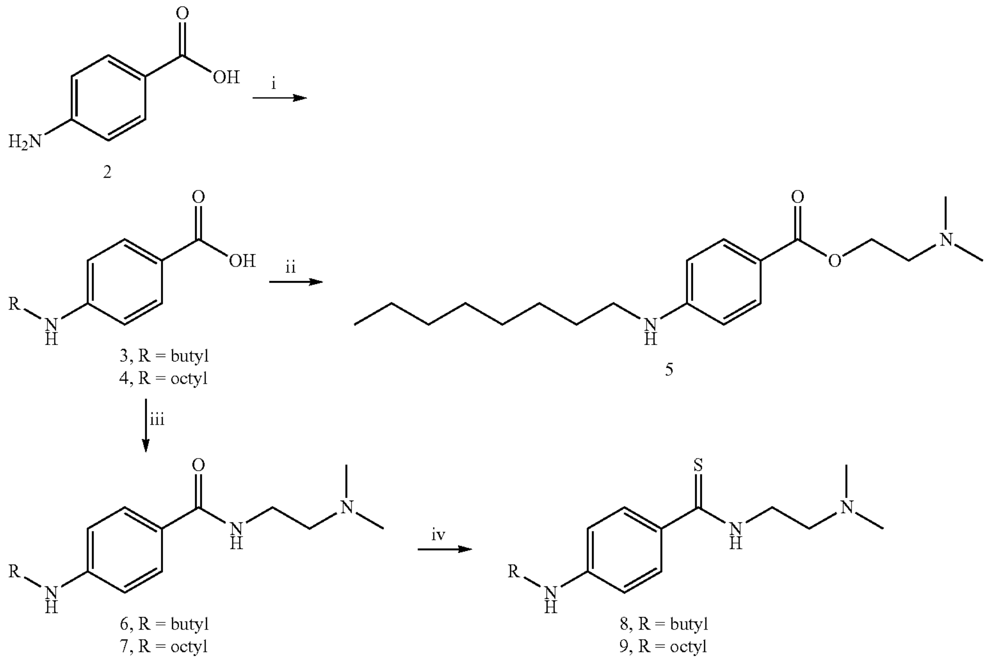

Reagents and conditions:
(i) butanal or octanal, α-picoline-borane, MeOH, room temperature, 16-24 hours (88% yield for compound 3, 94% yield for compound 4)
(ii) CDI, DME, 60° C., 2 hours, followed by 2-(dimethylamino)ethanol, NaH, 60° C. to room temp, 16-24 hours (95% yield)
(iii) CDI, DME, 60° C., 2 hours, followed by N',N'-dimethylethane-1,2-diamine, NaH, 60° C. to room temp, 16-24 hours (93%, yield for compound 6, 87% yield for compound 7)
(iv) Lawesson's reagent, toluene, reflux 2.5 hours (26% yield for compound 8, 73% yield for compound 9).

and compound (5 μM). Time scale is shown in the lower left-hand corner of the panel and FIG. 1, and the zero current level is indicated by the dotted line.

Figure 4:
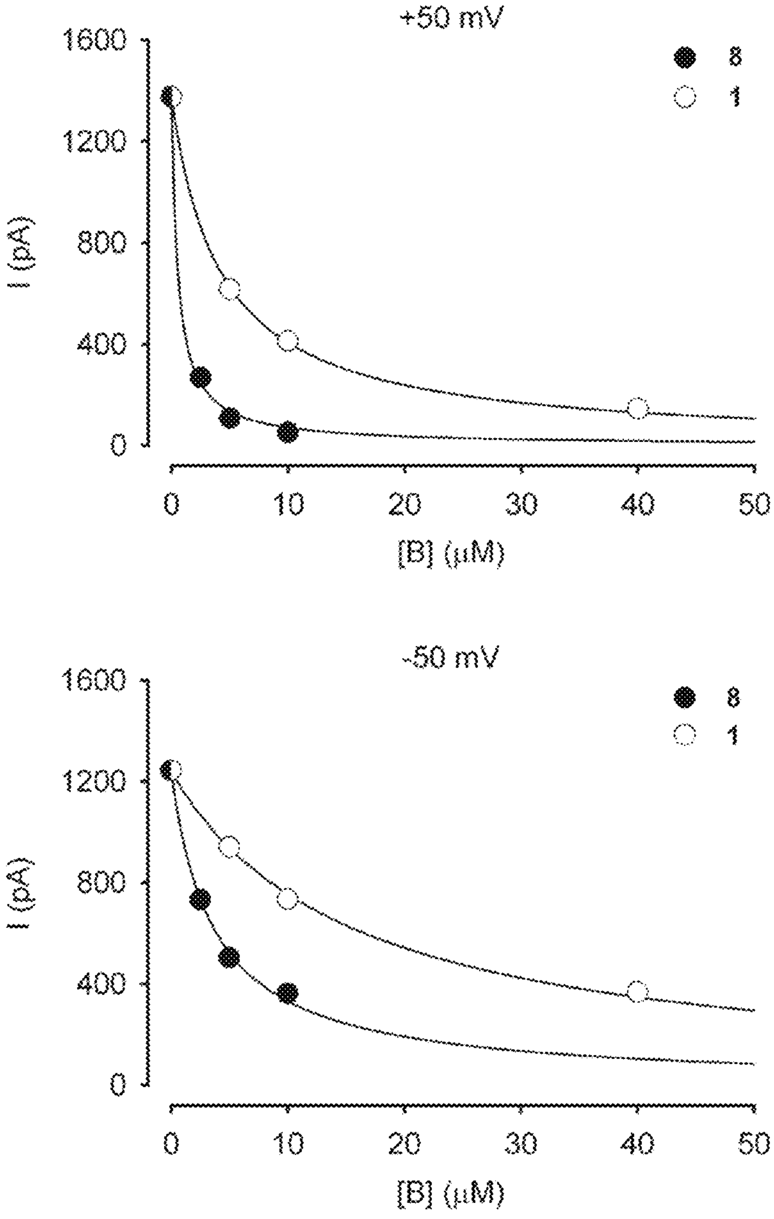
FIG. 4 is a set of graphs of currents obtained from a concentration series of compounds 1 (white) and 8 (black) plotted against compound concentration. The solid line indicates the fit of the equation for block at a single binding site. The top panel is determined at +50 mV, the bottom panel at −50 mV.

FIG. 4 depicts currents obtained from a concentration series of compound 1 (white) and compound 8 (black) plotted against compound concentration on the x-axis. The solid line indicates the fit of the equation for block at a single binding site. $K_D$ values determined from the fit of the equation were 4.2 μM at +50 mV and 15.6 μM at −50 mV for compound 1, and 0.5 μM at +50 mV and 3.7 μM at −50 mV for compound 8.

Figure 3:
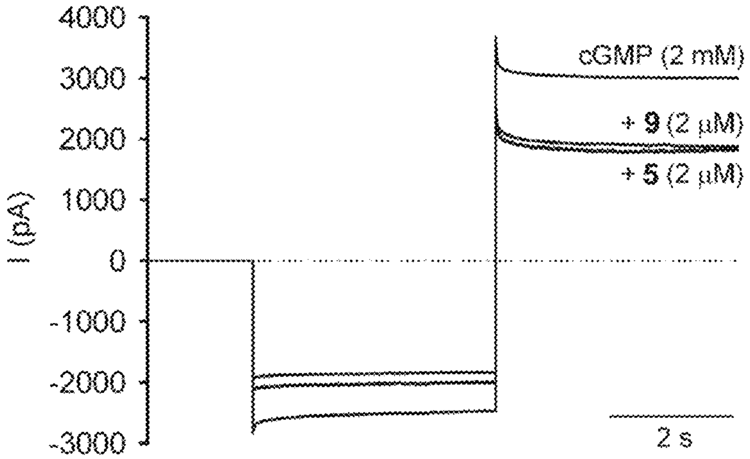
FIG. 3 is a graph showing currents were elicited by the voltage step protocol of FIG. 1 in the presence of 2 mM cGMP or 2 mM cGMP and the indicated concentration of compound 5 or compound 9.
Figure 5:
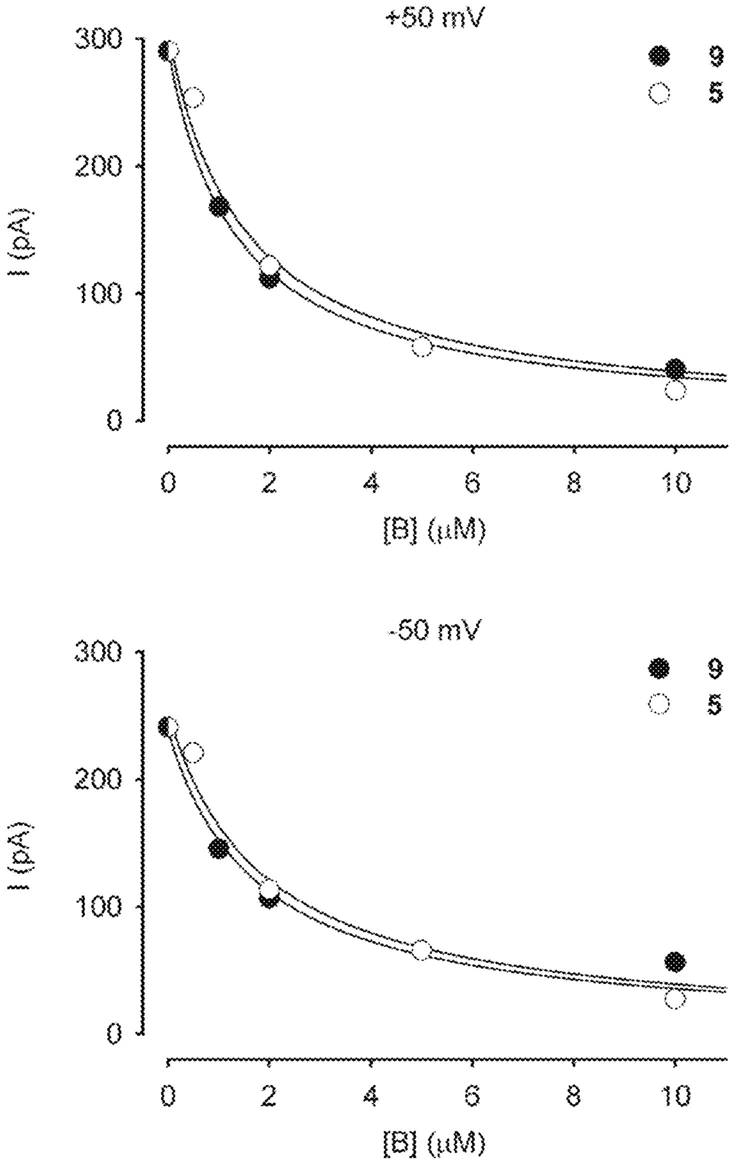
FIG. 5 is a set of graphs of currents obtained from a concentration series of compounds 5 (white) and 9 (black) plotted against compound concentration. The solid line indicates the fit of the equation for block at a single binding site. The top panel is determined at +50 mV, the bottom panel at −50 mV.

FIG. 3 and FIG. 5 depict heteromeric rod CNG channel block by compound 5 and compound 9. FIG. 3 depicts leak-subtracted currents from a representative excised inside-out patch from oocytes expressing heteromeric rod CNG channels. Currents were elicited by a voltage step protocol from 0 to −50 mV to +50 mV (see FIG. 1) in the presence of 2 mMcGMP or 2 mMcGMP and compound (5 μM). Time scale is shown in the lower left-hand corner of the panel and FIG. 1, and the zero current level is indicated by the dotted line. FIG. 5 depicts currents obtained from a concentration series of compound 5 (white) and compound 9 (black) are plotted against compound concentration. Solid line indicates the fit of the equation for block at a single binding site. $K_D$ values determined from the fit of the equation were 1.5 μM at +50 mV and 1.8 μMat-50 mV for compound 5, and 1.3 μM at +50 mV and 1.8 μM at −50 mV for compound 9

Example 2

CNG Channel Block at Saturating cGMP

Figure 2:
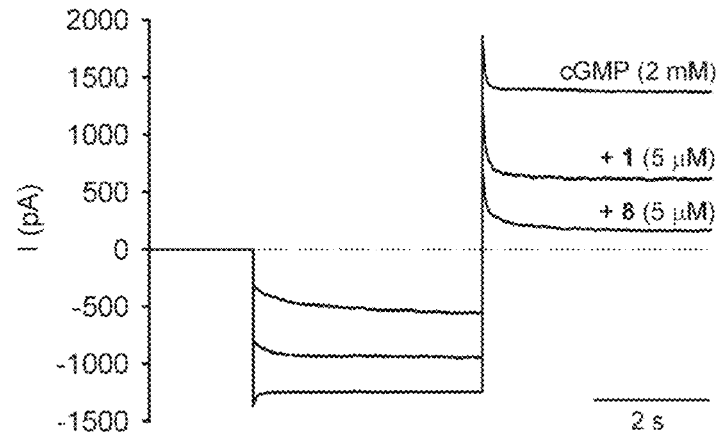
FIG. 2 is a graph showing currents were elicited by the voltage step protocol of FIG. 1 in the presence of 2 mM cGMP or 2 mM cGMP and the indicated concentration of compound 1 or compound 8.

FIG. 2 and FIG. 4 depict the results of a heteromeric rod CNG channel block by compound 1 and compound 8. Specifically, FIG. 2 depicts leak-subtracted currents from a representative excised inside-out patch from oocytes expressing heteromeric rod CNG channels. Currents were elicited by a voltage step protocol from 0 to −50 to +50 mV (See FIG. 1) in the presence of 2 mM cGMP or 2 mM cGMP The effectiveness of retinal rod CNG channel current block by the disclosed compounds was tested in *Xenopus* oocyte preparations. Excised, inside-out patches pulled from oocytes expressed heteromeric rod CNG channels consisting of CNGA1 and CNGB1 subunits. This was verified by substantial block of 2 mM cGMP-induced currents with 20 μM l-cis-diltiazem (74.2±5.8% at Vm=+50 mV) (Korschen H G et al, Neuron 15, 627-636 (1995), incorporated by reference herein.) Each compound's apparent affinity for the heteromeric CNG channel was determined under maximal channel activation (2 mM cGMP). CNG channel currents were elicited by a voltage step protocol to −50 and +50 mV (FIG. 1). The apparent $K_D$ value at each membrane potential was estimated first by determining $I_{+B}$ and $I_{-B}$ at steady state, where $I_{+B}$ is the current in the presence of blocker and $I_{-B}$ is current in the absence of blocker, for different blocker concentrations ([B]).

The following equation for block at a single binding site was fit to the data to obtain $K_D$:

$$I_{+B}=I_{-B}K_D/(K_D+[B])$$

Representative traces for CNG channel currents at positive and negative membrane potentials activated by 2 mM cGMP, are shown for compound 1 and compound 8 (FIG. 2) and compound 5, and compound 9 (FIG. 3). Compound 8 is a higher affinity CNG channel blocker relative to compound 1 at both positive and negative membrane potentials (FIG. 2). In contrast, compound 9 (having the same headgroup linkage as compound 8) has a similar CNG channel affinity compared to compound 5. All compounds tested exhibited voltage dependent blocking, although compounds 5, 7, and 9 were appreciably less voltage dependent than compound 1, 6, and 8.

Figure 6:
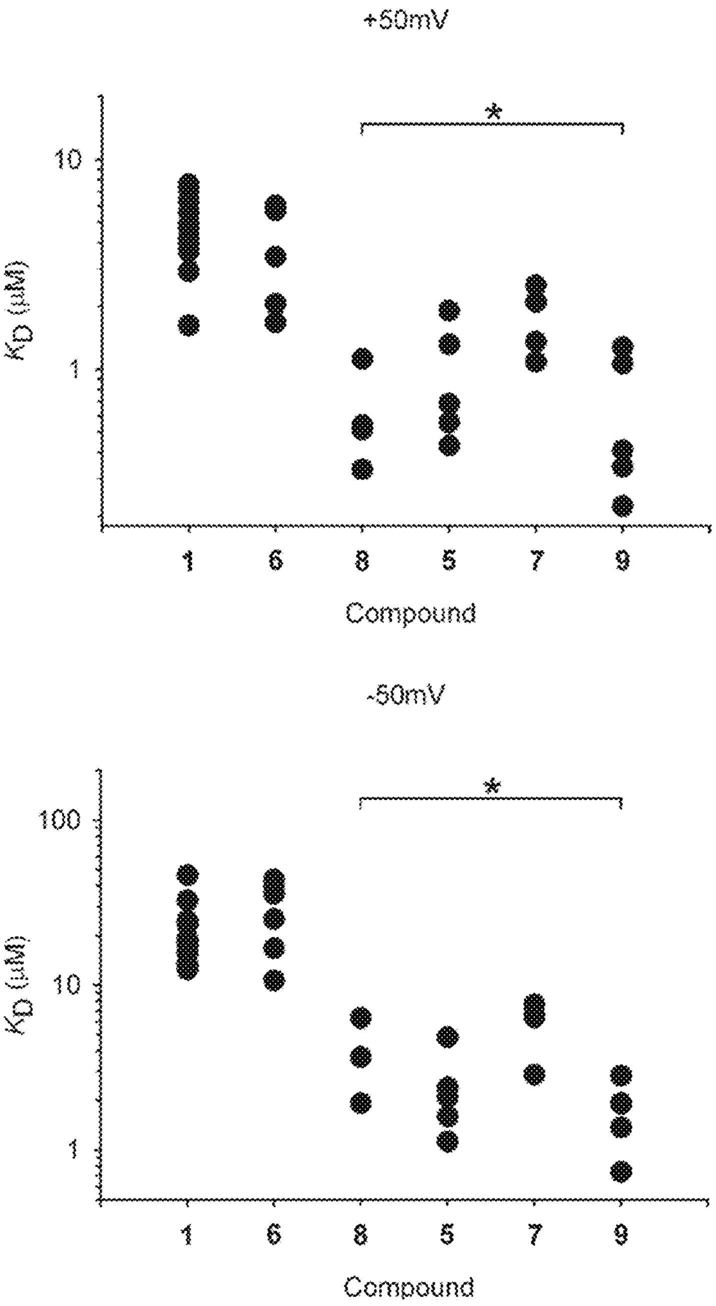
FIG. 6 is a plot of $K_D$ values determined from all experimental patches. Plots show all $K_D$ values determined at +50 mV (upper panel) and −50 mV (lower panel). Solid horizontal brackets with asterisks indicate groups significantly different from compound 1 using the Holm-Sidak method for multiple pairwise comparisons; P<0.01.
Figure 7:
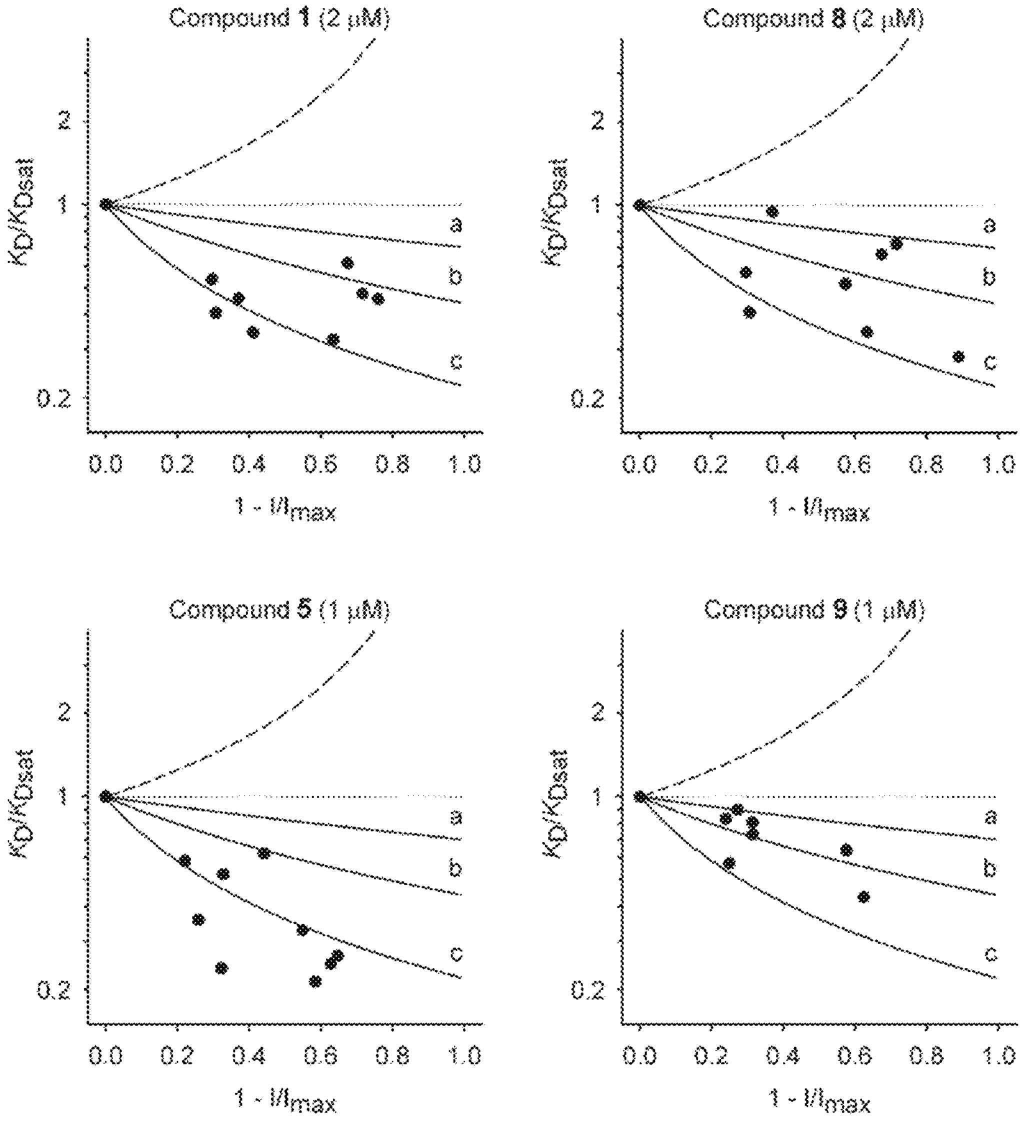
FIG. 7 is a set of plots showing the relationship of all $K_D$ values determined for compounds 1 (2 μM), 8 (2 μM), 5 (1 μM), and 9 (1 μM) at subsaturating cGMP (50 or 100 μM) at +50 mV normalized to $K_D$ values determined at saturating cGMP (2 mM), versus $1-I/I_{max}$, which is related to the fraction of closed channels. $K_D$ values at saturating cGMP were corrected for ion accumulation. Solid lines indicate simulations for exclusive closed channel blockers, using $K_D/K_{Dsat}=(1-F_{sat})/(1-F_{sat}I/I_{max})$, where $F_{sat}$ is the estimated fraction of open heteromeric rod channels in saturating cGMP assuming $F_{sat}=0.3$ (a), 0.56 (b), or 0.78 (c). The dotted line is a simulation for a blocker with no preference for state, or $K_D/K_{Dsat}=1$. The dashed line is a simulation for an exclusive open channel blocker, using $K_D/K_{Dsat}=(I/I_{max})^{-1}$.

A small transient decay in current attributed to an ion accumulation effect was seen with each voltage step with large currents (typically >1 nA) (Zimmerman A L et al, *Biophys J* 54, 351-355 (1995), incorporated by reference herein.) Corrections for ion accumulation did not substantially change previous $K_D$ estimates for compound 1 (6.8 μM corrected and 6.7 μM not corrected, both determined at +40 mV) (Strassmaier (2005) supra and Strassmaier (2008) supra). $K_D$ value estimates for ion accumulation for compounds 6, 7, 8, and 9 similarly did not change significantly when corrected for ion accumulation. As a result, the $K_D$ values reported herein were not corrected for ion accumulation. The $K_D$ values at both +50 and −50 mV for all compounds tested are plotted in FIG. 6. The mean $K_D$ values are summarized in Table 1, along with estimated log P values for each compound.

Amide substitution of the ester linkage of compound 1 (to generate compound 6) has little effect on the $K_D$ values, while the thioamide substitution unexpectedly improves the affinity for CNG channels (compound 8). Amide (compound 7) and thioamide (compound 9) substitutions of compound 5 have little effect on $K_D$.

Example 3

State Dependence of Block

Compound 1 has been reported to preferentially block CNG channels in the closed conformation, and its ability to block CNG channels improves with half-maximal channel activation (Fodor, 1997 supra). The apparent $K_D$ values were determined at both positive and negative potentials for CNG channel currents activated by saturating (2 mM) and subsaturating concentrations of cGMP (50 and 100 μM). The $K_D$ values for all compounds were lower at subsaturating cGMP than at saturating cGMP. The $K_D$ values of each of compounds 1, 8, 5, and 9 at subsaturating cGMP (+50 mV) normalized to the $K_D$ values at saturating cGMP are plotted against $1-I/I_{max}$, which is related to the fraction of closed channels in FIG. 6. The solid lines in FIG. 4 marked a, b, and c represent the expected relationship between $K_D$ and the fraction of closed channels for an exclusive closed channel blocker. Each of a, b, and c uses one estimate for the probability of closed heteromeric retinal rod channels at saturating cGMP. The simulations are described in the following references: Matthews G et al, *J Physiol* 403, 389-405 (1988); Taylor W R & Baylor D A, *J Physiol* 483 567-582 (1995); and Bucossi G et al, *Biophys J* 72, 1165-1181 (1997), all of which are incorporated by reference herein. The dotted line represents a simulation of a blocker with no preference as to conformational of the channel. The dashed line represents a simulation for an exclusive open channel blocker.

Despite inherent variability in the relationships between $K_D$ values and fractional current, the data for compounds 1, 5, 8, and 9 better fit the results expected of a closed channel blocker. Therefore, all of compounds 1, 5, 8, and 9 all are likely to block CNG channels by the same mechanism.

Example 4

Resistance to In Vitro Hydrolysis

In addition to the higher affinity for CNG channels by compound 8 relative to compounds 1 and 5, the amide and thioamide linkage substitutions should provide an improvement for many in vivo applications or tissue preparations to a tetracaine-based CNG channel blocker in terms of biological stability. Compound 1 is rapidly hydrolyzed by butyrylcholinesterase in the bloodstream. Butyrylcholinesterase purified from human blood serum was used to test the resistance of the disclosed compounds to hydrolysis. Results are shown in Table 1.

TABLE 1

$K_D$ values, estimated Log P, and rate of in vitro serum cholinesterase hydrolysis for tetracaine (compound 1), compound 5, and compounds 6, 7, 8, and 9 disclosed herein. Structures are depicted in the expected predominant protonation state at pH 7.6. Log P is calculated for the unprotonated forms using ALOGPS 2.1 (Virtual Computational Chemistry Laboratory)

| Compound # | $K_{D(+50)}$ (μM) | $K_{D(-50)}$ (μM) | n | Log P | Hydrolysis rate nmol/min · mg |
|---|---|---|---|---|---|
| 1 | 4.9 ± 1.8 | 21.8 ± 8.6 | 16 | 3.1 | 132 ± 10 |
| 5 | 1.0 ± 0.6 | 2.4 ± 1.4 | 5 | 5.1 | 213 ± 31 |
| 6 | 4.4 ± 2.0 | 28.6 ± 13.1 | 7 | 2.3 | 8.4 ± 3.5 |
| 7 | 1.6 ± 1.5 | 3.7 ± 1.5 | 4 | 4.3 | 1.2 ± 0.5 |
| 8 | 0.6 ± 0.3 | 3.9 ± 1.8 | 4 | 2.8 | ND |
| 9 | 0.7 ± 0.5 | 1.8 ± 0.8 | 5 | 4.8 | ND |

ND = no hydrolysis detected.

As shown in Table 1, the amide linkage substitutions of compounds 6 and 7 provided substantial resistance to hydrolysis. The thioamide linkage substitutions of compound 8 and compound 9 improved hydrolysis resistance of to such a degree that no hydrolysis product was detected even after a 24-hour incubation in the presence of butyrylcholinesterase.

The amide linkages of compounds 6 and 7 could potentially be susceptible to hydrolysis by proteases. However, the broad-spectrum, nonspecific endopeptidases chymotrypsin and proteinase K, were not able to generate any detectable hydrolysis products for any of compounds 6, 7, 8, or 9. Hydrolysis products of 4-nitrophenyl acetate and BSA were detected as positive controls.

Example 5

Experimental Methods

Retinal Rod CNG Channel Expression in Oocytes:

Ovaries were surgically removed from adult *Xenopus laevis* females (Xenopus Express; Brooksville, Fla.) anesthetized with ice-cold 0.1% tricaine and 0.1% NaHCO3 solution. Oocytes were chemically released from ovarian follicles in $Ca^{2+}$-free Barth's solution (88 mM NaCl, 1 mM KCl, 2.4 mM NaHCO3, 0.82 mM MgSO4, 7.5 mM Tris, 2.5 mM sodium pyruvate, 100 U/mL penicillin, and 100 μg/mL streptomycin, pH 7.4) containing 0.1 U/mL Liberase Blendzymes (Roche, Indianapolis, Ind.). Stages IV and V oocytes were visually sorted and stored in ND-96 (96 mM NaCl, 2 mM KCl, 1.8 mM CaCl2, 1 mM MgCl2, 5 mM HEPES, 2.5 mM sodium pyruvate, 100 U/mL penicillin, and 100 μg/mL streptomycin, pH 7.4) at 16° C. Oocytes were co-injected the following day with 33 ng of CNGA1 and 67 ng of CNGB1 cRNA (2:1) synthesized from linearized pGEM-HE expression vectors containing the channel subunit cDNA sequence (Strassmaier T & Karpen J, J Med Chem 50, 4186-4194, (2007), incorporated by reference herein) using T7 mMESSAGE mMACHINE® (Ambion, Austin, Tex.). Injected oocytes were incubated at 18° C. the first day and 16° C. for the remaining days.

Electrophysiological Recordings:

Recordings from inside-out excised patches were made 3-7 days after oocyte injection on an Axopatch 1D® amplifier (Axon Instruments, Foster City, Calif.). Briefly, oocyte vitelline membranes were removed in solution containing 200 mM K aspartate, 20 mM KCl, 1 mM MgCl2, 10 mM EGTA, 10 mM HEPES, pH 7.4. Oocytes were placed in a recording chamber in a solution containing 130 mM NaCl, 2 mM HEPES, 0.02 mM EDTA, 1 mM EGTA, pH 7.6, and borosilicate glass electrodes (1-3 MΩ) were filled with identical solution. Macroscopic currents were filtered at 1 kHz and sampled at 2 kHz using pCLAMP 8.0® software (Axon Instruments). Channels were either fully activated with 2 mM or partially activated with 50 and 100 μM cGMP. Solutions containing different tetracaine derivatives were exchanged using a RSC-100® rapid solution changer (Molecular Kinetics, Pullman, Wash.). Glass syringes and Teflon tubing were used to minimize the binding of compounds to surfaces; concentrations passing through the perfusion system were verified by absorbance. Current traces were digitally filtered at 300 Hz (Gaussian) and averaged using Clampfit 8.2® software. Currents in the absence of cGMP were subtracted from all currents analyzed. KD values were determined and expressed as the mean±SD.

In Vitro Ester Hydrolysis:

All enzymatic assays were performed with 50 μM compound in 0.1M phosphate buffer, pH 7.4, at 37° C. with stirring, unless otherwise noted. Butyrylcholinesterase stock solutions from human serum (Sigma, St. Louis, Mo.) were prepared at 100 U/mL in 0.1 M phosphate buffer, pH 7.4, and stored at −20° C. until use. Hydrolysis was monitored on an 8452A diode array spectrophotometer (Hewlett-Packard). Product peak wavelength absorption was immediately monitored upon addition of compound. Absorbances for complete hydrolysis were determined when there were no further detectable changes. Hydrolysis rates were calculated based on the changes in absorbance during the first 1 minute of hydrolysis (compounds 1 and 5) or first the first 9 minutes (compounds 6 and 7) and were adjusted to the absorbance at the completion of the reaction. All hydrolysis assays were performed in triplicate, and final rate constants are expressed as the mean±SD of the three individually determined rate constants. In some experiments with compound 1, samples were taken at the beginning and end of the assay to verify the hydrolysis product and the completion of the reaction by HPLC. These samples were compared to compounds 1 and 3 on a C18 column eluted with 0.1% TFA in water/acetonitrile. Activity of chymotrypsin (bovine, Worthington Biochemical Co., 190 μg/mL) was verified with 90 μM 4-nitrophenyl acetate in 0.1 M HEPES solution, pH 6.5, at 37° C. with stirring. Hydrolysis product was monitored at 404 nm for 10 min. Activity of proteinase K (from Engyodontium album, Sigma, 165 μg/mL) was verified with 16.5 mg/mL bovine serum albumin in 0.1 M phosphate buffer, pH 7.4, at 37° C. Samples were taken at time point increments up to 2 hours when the reaction reached completion. Samples were analyzed with 12% SDS-PAGE, stained with 0.1% Coomassie Blue.

Statistical Analysis:

Statistical comparison between groups was made using a one-way repeated-measures ANOVA and the Holm-Sidak post hoc method for multiple pairwise comparisons. Statistical significance was accepted at $P<0.01$.

Example 6

Compound Preparation and Characterization, Compounds 6, 7, 8, and 9

Reagents, including compounds 1 and 2, were obtained from Sigma-Aldrich and were used without further purification. TLC was performed on glass backed silica plates and eluted in a mixture of 5-10% methanol and 90-95% dichloromethane. Plates were visualized using short wave UV light and $KMnO_4$. Crude compounds were initially purified using column chromatography, which was packed with normal phase silica gel and eluted using either ethyl acetate/hexane or methanol/dichloromethane mixtures. Trace impurities were removed by reversed-phase HPLC on an Xterra Prep RP8 column, 19 mm×100 mm, 5 μm (Waters, Milford, Mass.), with a water-methanol gradient (5 mM ammonium acetate, pH 5), monitored at 214 and 310 nm to yield final products. Purity was assessed to be greater than 95% with an Xterra Analytical RP8 column, 4.6 mm×250 mm, 5 μm, under similar conditions and monitoring. $^1$H and $^{13}$C NMR spectra were obtained using a Bruker 500 MHz FT-NMR spectrometer. ESI-MS was performed on a Thermo Finnigan TSQ Classic® mass spectrometer.

4-(Butylamino)benzoic Acid (Compound 3)

Compound 2 (about 3 mmol) was dissolved in 15 mL of methanol with R-picoline-borane (1.1 mol equiv) and butanal (1.1 mol equiv). The mixture was stoppered with a vent needle and stirred overnight at room temperature. After 16-24 hours, solvent was removed in vacuo, 10 mL 1 M HCl was added to the flask, and the mixture was stirred at room temperature for an additional 30 minutes. The pH was adjusted to neutral using $NaHCO_3$, and the intermediate product was extracted with ethyl acetate (2×60 mL). The organic layer was washed with brine (1×45 mL), dried with magnesium sulfate, filtered, removed in vacuo, and subsequently purified via column chromatography with 30% ethyl acetate in hexane to yield compound 3 (88%) as a white powder. $^1$H NMR (500 MHz) ($CD_3OD$): δ 7.92 (d, J=8.8 Hz, 2H), 6.55 (d, J=8.8 Hz, 2H), 3.18 (t, J=7.2 Hz, 2H), 1.63 (m, 2H), 1.44 (m, 2H), 0.97 (t, J=7.4 Hz, 3H). 13C NMR (125 MHz) ($CD_3OD$): δ 172.6, 153.1, 132.7, 117.3, 111.6, 43.4, 31.7, 20.5, 14.1.

4-(Octylamino)benzoic Acid (Compound 4)

The product was prepared as described for compound 3 (above) with octanal to yield compound 4 (94%) as a white powder. $^1$H NMR (500 MHz) (CD3OD): δ 7.92 (d, J=8.9 Hz, 2H), 6.55 (d, J=8.9 Hz, 2H), 3.17 (t, J=7.2 Hz, 2H), 1.63

(m, 2H), 1.25-1.41 (m, 10H), 0.89 (t, J=7.0 Hz, 3H). $^{13}$C NMR (125 MHz) ($CD_3OD$): δ 172.6, 153.1, 132.7, 117.3, 111.6, 43.7, 32.1, 29.7, 29.6, 29.5, 27.4, 23.0, 14.4.

2-(Dimethylamino)ethyl 4-(Octylamino)benzoate (Compound 5)

In a flame-sealed flask, Compound 4 (about 0.50 mmol) and CDI (1.5 mol equiv) were dissolved in 3.0 mL of 1,2-dimethoxyethane (DME). The solution was stirred at 60° C. for approximately 2 h under argon. 2-(Dimethylamino)-ethanol (3 mol equiv) was added to the solution followed by a small quantity of NaH (~2 mg). The flask was allowed to cool to room temperature and react for an additional 16-24 hours. The reaction was worked up by dissolving it in 100 mL of chloroform and washing with water (2×60 mL) and brine (1×60 mL). The organic layer was dried with sodium sulfate, filtered, removed in vacuo, and subsequently purified via column chromatography with 30% ethyl acetate in hexane to yield compound 5 (95%) as a white powder. $^1$H NMR (500 MHz) (CD3OD): δ 7.83 (d, J=8.9 Hz, 2H), 6.59 (d, J=8.7 Hz, 2H), 4.58 (t, J=5.0 Hz, 2H), 3.57 (t, J=5.0 Hz, 2H), 3.14 (t, J=7.1 Hz, 2H), 3.00 (s, 6H), 1.63 (m, 2H), 1.25-1.5 (m, 10H), 0.90 (t, J=6.8 Hz, 3H). $^{13}$C NMR (125 MHz) ($CDCl_3$): δ 166.8, 152.2, 131.6, 117.9, 111.3, 62.3, 58.0, 45.9, 43.4, 31.8, 29.4, 29.3, 29.2, 27.1, 22.7, 14.1. ESI-MS: m/z 321.1 MH+. Mp: 40-41° C.

4-(Butylamino)-N-(2-(dimethylamino)ethyl)benzamide (compound 6)

In a flame-sealed flask, compound 3 (about 0.50 mmol) and CDI (1.5 mol equiv) were dissolved in 3.0 mL of DME, and the mixture was stirred at 60° C. for approximately 2 h under argon. N',N'-Dimethylethane-1,2-diamine (3 mol equiv) was added to the solution followed by a small quantity of NaH (about 2 mg). The flask was allowed to cool to room temperature and react for an additional 16-24 hours. The reaction was worked up by dissolving it in 100 mL of chloroform and washing with water (2×60 mL) and brine (1×60 mL). The organic layer was dried over sodium sulfate, filtered, removed in vacuo, and subsequently purified via column chromatography with 30% ethyl acetate in hexane to yield compound 6 (93%) as pale brown oil. $^1$H NMR (500 MHz) (CD3OD): δ 8.13 (d, J=8.8 Hz, 2H), 7.61 (d, J=8.8 Hz, 2H), 3.82 (t, J=5.9 Hz, 2H), 3.44 (m, 4H), 3.02 (s, 6H), 1.76 (m, 2H), 1.50 (m, 2H), 1.02 (t, J=7.4 Hz, 3H). $^{13}$C NMR (125 MHz) ($CD_3OD$): δ 170.2, 141.8, 135.8, 131.7, 124.0, 59.5, 53.1, 44.8, 37.3, 30.3, 21.6, 14.8. ESI-MS: m/z 264.22 MH$^+$.

4-(Octylamino)-N-(2-(dimethylamino)ethyl)benzamide (Compound 7)

The product was prepared as described for compound 6 using compound 4 to yield compound 7 (87%) as pale brown oil. $^1$HNMR (500 MHz) (CDCl3): δ 7.66 (d, J=8.8 Hz, 2H), 6.99 (br, 1H), 6.55 (d, J=8.8 Hz, 2H), 3.98 (br, 1H), 3.57 (m, 2H), 3.13 (t, J=7.1 Hz, 2H), 2.68 (t, J=5.7 Hz, 2H), 2.40 (s, 6H), 1.61 (m, 2H), 1.25-1.40 (m, 10H), 0.88 (t, J=6.9 Hz, 3H). $^{13}$C NMR (125 MHz) (CDCl3): δ 167.8, 151.4, 129.1, 122.4, 111.8, 58.4, 51.1, 45.2, 43.8, 36.9, 32.1, 29.7, 29.6, 27.4, 23.0, 14.4. ESI-MS: m/z 320.08 MH$^+$.

4-(Butylamino)-N-(2-(dimethylamino)ethyl)benzothioamide (Compound 8)

In a flame-sealed flask, compound 6 (about 0.25 mmol) was dissolved in 5 mL of dry toluene with Lawesson's reagent (1 mol equiv) and refluxed under argon for 2.5 h. The mixture was dissolved in 20 mL of ethyl acetate, washed with water (2×20 mL), dried over sodium sulfate, and subsequently purified via column chromatography with 10% methanol in dichloromethane to yield 8 (26%) as yellow oil. $^1$HNMR (500 MHz) ($CDCl_3$): δ 8.64 (br, 1H), 7.79 (d, J=9 Hz, 2H), 6.51 (d, J=9 Hz, 2H), 4.03 (br, 1H), 3.97 (m, 2H), 3.14 (t, J=7.1 Hz, 2H), 2.85 (m, 2H), 2.44 (s, 6H), 1.60 (m, 2H), 1.42 (m, 2H), 0.96 (t, J=7.4 Hz, 3H). $^{13}$C NMR (125 MHz) (CDCl3): δ 197.6, 151.7, 129.3, 129.2, 111.7, 57.0, 45.1, 43.5, 43.2, 31.7, 20.5, 14.2. ESI-MS: m/z 280.1 MH$^+$.

4-(Octylamino)-N-(2-(dimethylamino)ethyl)benzothioamide (Compound 9)

The product was prepared as described for compound 8 using compound 7 to yield compound 9 (73%) as a yellow oil. $^1$H NMR (500 MHz) (CDCl3): δ 8.41 (br, 1H), 7.76 (d, J=8.8 Hz, 2H), 6.52 (d, J=8.8 Hz, 2H), 4.02 (br, 1H), 3.90 (m, 2H), 3.14 (t, J=7.1 Hz, 2H), 2.72 (t, J=5.4 Hz, 2H), 2.35 (s, 6H), 1.62 (m, 2H), 1.25-1.40 (m, 10H), 0.88 (t, J=7.0 Hz, 3H). $^{13}$C NMR (125 MHz) ($CDCl_3$): δ 197.4, 151.6, 129.4, 129.2, 111.8, 56.9, 51.2, 45.2, 43.8, 43.6, 32.2, 29.7, 29.6, 27.4, 23.0, 14.5. ESI-MS: m/z 336.13 MH$^+$.

Examples 7-9 pertain to compounds having the structure:

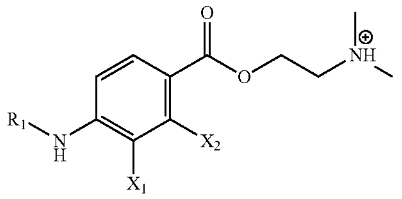

wherein $R_1$ is alkyl, $X_1$ is H, nitro, methoxy, methyl, or halo and wherein $X_2$ is H or halo so long as $X_1$ and $X_2$ are not both H.

Example 7

Synthesis of Series 12 and Series 14 Compounds

A set of aromatic substituted derivatives of tetracaine (compound 1) as well as a higher affinity octyl-tail derivative (indicated as compound 2 in the accompanying scheme, but compound 5 above) were synthesized. Electron-donating ($CH_3$, $CH_3O$) and electron-withdrawing (F, Cl, Br, $NO_2$) groups were added, located meta or ortho to the ester linkage. Scheme 1 outlines the synthesis of the eleven novel derivatives. Intermediates 11a and 13a were synthesized from 4-fluoro-3-nitrobenzoic acid (3a) by a nucleophilic aromatic substitution with N-butylamine or N-octylamine (Skinner P J et al, *Bioorg Med Chem Lett* 17, 6619, (2007), incorporated by reference herein). Intermediates 11b, 11c, 13b, 13c, 13e, 13f, and 13g were obtained by reductive amination of derivatives of 4-aminobenzoic acid (4b, 4c, 4e, 4f, and 4g) with butanal or octanal. The free carboxylic acid of the resulting alkylated intermediates (11 and 13) was then activated by 1,10-carbonyldiimidazole and reacted with 2-(dimethylamino)ethanol to yield target compounds 12a, 12b, and 12c and 14a, 14b, 14c, 14e, 14f, and 14g. Compounds 12d and 14d were made from compounds 1 and 2 using N-chlorosuccinimide, via a synthesis adapted from Lazar et al, *J Med Chem* 47, 6973 (2004), incorporated by reference herein.

Scheme 2:

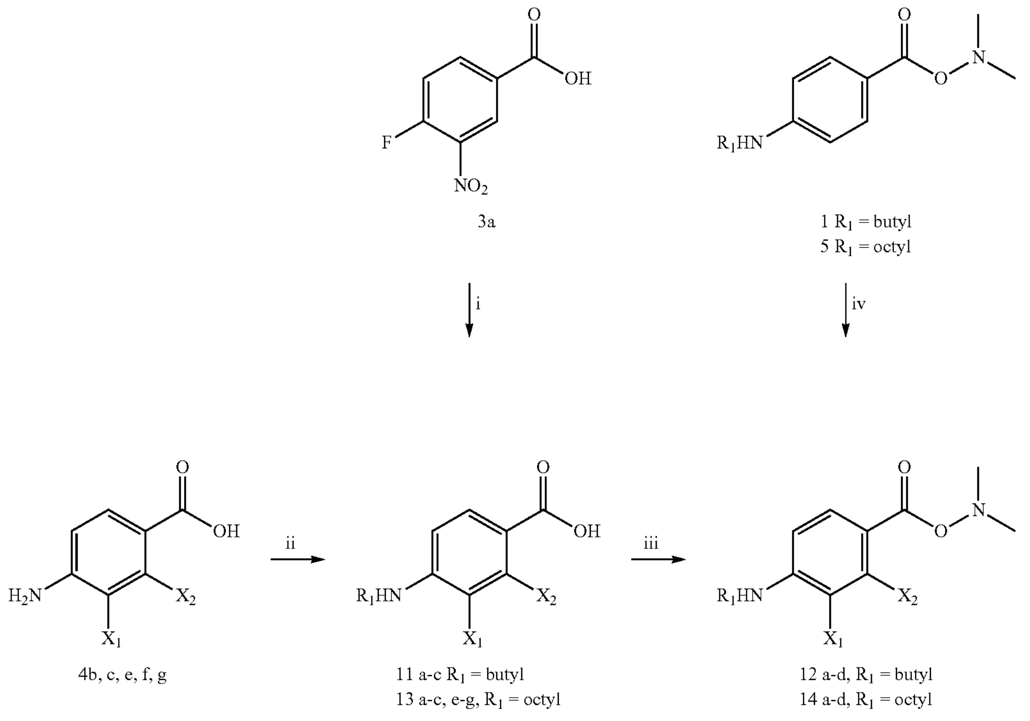

3a

1 $R_1$ = butyl
5 $R_1$ = octyl 4b, c, e, f, g 11 a-c $R_1$ = butyl
13 a-c, e-g, $R_1$ = octyl 12 a-d, $R_1$ = butyl
14 a-d, $R_1$ = octyl $X_1$ and $X_2$ are defined in Tables 1 and 2;
Reagents and conditions:
(i) N-butylamine/N-octylamine, H2O, NaHCO3, 3 h at 150° C.;
(ii) butanal/octanal, a picolineborane, MeOH, 1-24 hours at room temperature;
(iii) 1,10-carbonyldiimidazole, 1,2-dimethoxyethane(glyme), 2 hours at 60° C. followed by 2-(dimethylamino)ethanol, NaH, 16-24 hours at room temperature;
(iv) N-chlorosuccinimide, acetonitrile, 24 hour reflux.

Example 8

Blocking of CNG Channels by Series 12 and Series 14 Compounds

Heteromeric retinal CNG channels comprised of CNGA1 and CNGB1 subunits were expressed in *Xenopus laevis* oocytes as described in Andrade A L et al, J Med Chem 54, 4904 (2011) and Quandt F N et al Neuroscience 42, 629 (1991) (both of which are incorporated by reference herein.) CNG channel currents were elicited with 2 mM cGMP at both positive (+50 mV) and negative (−50 mV) membrane potentials.

Electrophysiological methods as well as data analysis are as described in Examples 1-5 above. Potency of CNG channel block was assessed by fitting current amplitudes to the equation for block at a single binding site (see Tables 2 and 3). Apparent KD values at +50 and −50 mV for tetracaine (compound 1) and derivatives 12a, 12b, 12c, and 12d with various substituents at the 3-position are summarized in Table 2. Compound 12d was the only compound in this series to have a slightly higher apparent affinity for CNG channels than compound 1 at both membrane potentials.

TABLE 2

Dissociation constants for compounds of the following structure:

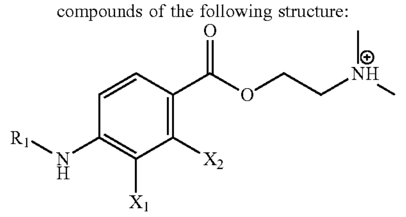

wherein $R_1$ is butyl, wherein $X_2$ is H, and wherein $X_1$ is as indicated in the table

| Compound ID | $X_1$ | $K_{D(+50)}$ (μM) | $K_{D(-50)}$ (μM) | n | $\sigma_p$ | $r_w$ (Å) |
|---|---|---|---|---|---|---|
| 1 | H | 4.9 ± 1.8 | 21.8 ± 8.6 | 16 | 0.00 | 1.20 |
| 12a | NO2 | 5.5 ± 3.2 | 19.6 ± 14.4 | 7 | 0.78 | 2.59 |
| 12b | OMe | 4.3 ± 0.8 | 18.3 ± 4.4 | 7 | −0.27 | 1.56 |
| 12c | Me | 7.8 ± 3.1 | 28.1 ± 13.4 | 7 | −0.17 | 1.72 |
| 12d | Cl | 3.0 ± 1.0 | 12.8 ± 4.1 | 7 | 0.23 | 1.75 |

The structure is depicted as the predominant protonation state at pH 7.6. The $K_{D(+50)}$ and $K_{D(-50)}$ are the apparent dissociation constants at +50 and −50 mV obtained from fits of the equation $I_{+B}/I_{-B}=K_D/K_D+[B]$, where the left side is current in the presence of blocker divided by current in the absence of blocker, and [B] is blocker concentration. $\sigma_p$ is the Hammett sigma constant at the para-position, which accounts for the net inductive and resonance effects. Positive values denote an electron-withdrawing substituent, and negative values an electron-donating substituent. $r_w$ (Å) is the Van der Waals radius; radius of a sphere that encloses the substituent.

In contrast to the butyl-tail derivatives, aromatic substituents in the octyl-tail series (Compounds 14a, 14b, 14c, 14d, 14e, 14f, and 14g) produced more dramatic results. Apparent $K_D$ values at +50 and −50 mV for the octyl-tail series (compounds 5, 14a-g) are presented in Table 3. Like compound 12d, compound 14d with a 3-Cl substituent had a higher affinity for CNG channels than compound 5; however the effect was more pronounced with an approximately six-fold improvement compared to the 1.6-fold improvement shown by compound 6d over compound 1. Different halogen substituents were introduced at the 3-position (compounds 14e and 14f), and a 2-Cl substituent ortho to the ester (compound 14g) was also introduced. All derivatives with halogen substituents, like compound 14d, had superior blocking potency compared to compound 5. The 14-series derivatives were up to eight-fold more potent than compound 5 and up to 50-fold more potent than tetracaine (compound 1). A derivative with a strong electron-donating 3-methoxy substituent (14b) blocked with roughly the same apparent affinity as compound 5, while a derivative with a 3-methyl group (14c), (a weak electron-donating substituent) had only marginally better apparent affinity than compound 5. The strongly electron-withdrawing nitro derivative (14a) deviated from the observed trend, blocking with a significantly lower apparent affinity than even compound 1.

TABLE 2

Disassociation constants for compounds of the following structure:

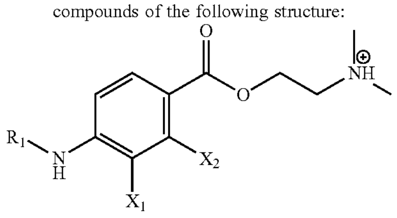

wherein $R_1$ is octyl and wherein $X_1$ and $X_2$ are as indicated in the table

| Compound ID | $X_1$ | $X_2$ | $K_{D(+50)}$ (μM) | $K_{D(-50)}$ (μM) | n | $\sigma_p$ | $r_w$[d] (Å) |
|---|---|---|---|---|---|---|---|
| 5 | H | H | 0.80 ± 0.50 | 1.72 ± 1.38 | 10 | 0.00 | 1.20 |
| 14a | $NO_2$ | H | 8.0 ± 5.8 | 12.6 ± 7.3 | 4 | 0.78 | 2.59 |
| 14b | OMe | H | 1.25 ± 1.23 | 3.0 ± 3.4 | 5 | −0.27 | 1.56 |
| 14c | Me | H | 0.50 ± 0.42 | 1.41 ± 0.84 | 5 | −0.17 | 1.72 |
| 14d | Cl | H | 0.14 ± 0.04 | 0.38 ± 0.16 | 4 | 0.23 | 1.75 |
| 14e | F | H | 0.20 ± 0.10 | 0.75 ± 0.86 | 5 | 0.06 | 1.47 |
| 14f | Br | H | 0.14 ± 0.03 | 0.24 ± 0.10 | 4 | 0.23 | 1.85 |
| 14g | H | Cl | 0.10 ± 0.09 | 0.22 ± 0.13 | 6 | 0.23 | 1.75 |

The structure is depicted as the predominant protonation state at pH 7.6. The $K_{D(+50)}$ and $K_{D(-50)}$ are the apparent dissociation constants at +50 and −50 mV obtained from fits of the equation $I_{+B}/I_{-B}=K_D/K_D+[B]$, where the left side is current in the presence of blocker divided by current in the absence of blocker, and [B] is blocker concentration. $\sigma_p$ is the Hammett sigma constant at the para-position, which accounts for the net inductive and resonance effects. Positive values denote an electron-withdrawing substituent, and negative values an electron-donating substituent. $r_w$ (Å) is the Van der Waals radius; radius of a sphere that encloses the substituent.

Example 9

Series 12 and 14 Compound Preparation and Characterization

Reagents, including compounds 1, 3a, 4b, c, e-g, were obtained from Sigma-Aldrich or TCl and were used without further purification. Thin layer chromatography was performed on glass backed silica plates and eluted in a mixture of 5-10% methanol and 90-95% dichloromethane. Plates were visualized using short wave ultraviolet light and $KMnO_4$. Crude compounds were initially purified using column chromatography, which was packed with normal phase silica gel and eluted using either ethyl acetate/hexane or methanol/dichloromethane mixtures. $^1H$ and $^{13}C$ NMR spectra were obtained using a Bruker 500 MHz spectrometer. Trace impurities were removed by reversed-phase HPLC on an Xterra Prep RP8 column, 19×100 mm, 5 μm (Waters, Milford, Mass.) with a water-methanol gradient (5 mM ammonium acetate, pH 5), monitored at 214 and 310 nm to yield final products. The purity of target compounds was assessed to be between 94% and greater than 99% with an Xterra Analytical RP8 column, 4.6×250 mm, 5 μm, under similar conditions and monitoring.

2-(dimethylamino)ethyl 4-(octylamino)benzoate (Compound 5)

Was synthesized as described in Andrade A L et al, *J Med Chem* 54, 4904 (2011), incorporated by reference herein.

4-(butylamino)-3-nitrobenzoic acid (Compound 11a)

Following a procedure adapted from Skinner P J et al, *Bioorg Med Chem Lett* 17, 6619 (2007), 4-fluoro-3-nitrobenzoic acid (~1 mmol) (3a), $NaHCO_3$ (2.1 mol eq), and N-butylamine (2.2 mol eq) were dissolved in 3 mL of water in a heavy walled reaction vessel. The reaction was heated to 150° C. and stirred for 3 h. The reaction was cooled to room temperature and 20 mL of 1 M HCl was added to the reaction. The mixture was dissolved in approximately 20 mL ethyl acetate, washed with water (2×15 mL) and brine (1×15 mL). The organic layer was dried over magnesium sulfate, filtered, removed in vacuo, and subsequently purified via column chromatography to yield 11a (70%).

4-(butylamino)-3-methoxybenzoic acid (Compound 11b)

4-amino-3-methoxybenzoic acid (4b) (~3 mmol) was dissolved in 15 mL methanol with α-picoline-borane (1.1 mol eq) and butanal (1.1 mol eq). The reaction was stoppered with a vent needle and stirred overnight at room temperature. After 16-24 h, solvent was removed in vacuo, 10 mL. A volume of 1 M HCl was added to the flask, and stirred at room temperature for an additional 30 min. The pH was adjusted to neutral using $NaHCO_3$ and the intermediate product was extracted with ethyl acetate (2×60 mL). The organic layer was washed with brine (1×45 mL), dried with magnesium sulfate, filtered, removed in vacuo, and subsequently purified via column chromatography with 30% ethyl acetate in hexane to yield 3 (84%).

4-(butylamino)-3-methylbenzoic acid (Compound 11c)

Prepared as described for 11b using 4-amino-3-methylbenzoic acid (4c) to yield 11c (62%).

2-(dimethylamino)ethyl 4-(butylamino)-3-nitrobenzoate (Compound 12a)

In a flame sealed flask, 11a (~0.50 mmol) and CDI (1.5 mol eq) were dissolved in 3.0 mL of DME. The solution was stirred at 60° C. for approximately 2 h under argon. 2-(Dimethylamino)ethanol (3 mol eq) was added to the solution followed by a small quantity of NaH (~2 mg). The flask was allowed to cool to room temperature and react for an additional 16-24 h. The reaction was worked up by dissolving it in 100 mL of chloroform and washing with water (2×60 mL) and brine (1×60 mL). The organic layer was dried with sodium sulfate, filtered, removed in vacuo, and subsequently purified via column chromatography with 30% ethyl acetate in hexane to yield 12a (92%) as dark yellow oil. $^1$H NMR (500 MHz) ($CDCl_3$) δ: 8.86 (d, J=2.0 Hz, 1H), 8.36 (br, 1H), 8.05 (dd, J=9.0, 2.0 Hz, 1H), 6.85 (d, J=9.0 Hz, 1H), 4.43 (t, J=5.8 Hz, 2H), 3.35 (m, 2H), 2.78 (t, J=5.7 Hz, 3H), 2.39 (s, 6H), 1.74 (pent, J=7.4 Hz, 2H), 1.48 (sext, J=7.5 Hz, 2H), 0.99 (t, J=7.4 Hz, 3H). $^{13}$C NMR (125 MHz) ($CDCl_3$) δ: 165.7, 147.8, 136.4, 131.1, 129.7, 116.9, 113.5, 62.5, 57.6, 45.6, 42.9, 30.8, 20.2, 13.8. ESI-MH$^+$: calculated, 310.37; observed, 310.18.

2-(dimethylamino)ethyl 4-(butylamino)-3-methoxybenzoate (Compound 12b)

Prepared as described for 12a using 11b to yield 12b (27%) as oily, brown-yellow crystals. $^1$H NMR (500 MHz) (MeOD) δ: 7.61 (dd, J=8.4, 1.8 Hz, 1H), 7.41 (d, J=1.8 Hz, 1H), 6.56 (d, J=8.4 Hz, 1H), 4.41 (t, J=5.5 Hz, 1H), 3.87 (s, 3H), 3.20 (t, J=7.1 Hz, 2H), 2.89 (t, J=5.5 Hz, 2H), 2.47 (s, 6H), 1.62 (pent, J=7.4 Hz, 2H), 1.44 (sext, J=7.4 Hz, 2H), 0.97 (t, J=7.4 Hz, 3H). $^{13}$C NMR (125 MHz) (MeOD) δ: 168.7, 147.1, 144.8, 126.2, 116.8, 110.8, 108.4, 62.3, 58.7, 56.1, 45.5, 43.5, 32.3, 21.3, 14.2. ESI-MH$^+$: calculated, 295.40; observed, 295.20.

2-(dimethylamino)ethyl 4-(butylamino)-3-methylbenzoate (Compound 12c)

Prepared as described for 12a using 11c to yield 12c (10%) as brown powder. $^1$H NMR (500 MHz) ($CDCl_3$) δ: 7.81 (dd, J=8.5, 2.0 Hz, 1H), 7.70 (d, 2.0 Hz, 1H), 6.55 (d, J=8.7 Hz, 1H), 4.64 (t, 5.0 Hz, 2H), 3.44 (t, 5.0 Hz, 2H), 3.22 (t, J=7.2 Hz, 2H), 2.90 (s, 6H), 2.13 (s, 3H), 1.66 (pent, J=7.4 Hz, 2H), 1.45 (sext, J=7.5 Hz, 2H), 0.97 (t, J=7.4 Hz, 3H). $^{13}$C NMR (125 MHz) ($CDCl_3$) δ: 166.2, 150.9, 131.7, 130.2, 120.8, 115.6, 108.3, 58.0, 56.0, 43.2, 43.1, 31.4, 20.3, 17.2, 13.9. ESI-MH$^+$: calculated, 279.40; observed, 279.21.

2-(dimethylamino)ethyl 4-(butylamino)-3-chlorobenzoate (Compound 12d)

Using a procedure adapted from Lazar et al., tetracaine hydrochloride (1) (2.27 mmol) was dissolved in 40 mL acetonitrile in a 2-necked round bottom flask. N-chlorosuccinimide (0.99 mol eq) was added and the mixture was stirred under reflux overnight (~24 h). The following day the reaction was cooled to room temperature and the solvent was removed in vacuo. The pH was raised to alkaline using $NaHCO_3$, extracted with ethyl acetate and washed with water (2×15 mL) and brine (1×15 mL). The organic layer was dried using magnesium sulfate, filtered, removed in vacuo, and subsequently purified via column chromatography with 30% ethyl acetate in hexane to yield 12d (75%) as brown-yellow oil. $^1$H NMR (500 MHz) ($CDCl_3$) δ: 7.92 (d, J=2.0 Hz, 1H), 7.84 (dd, J=8.6, 1.9 Hz, 1H), 6.60 (d, J=8.6 Hz, 1H), 4.77 (t, J=4.8 Hz, 1H), 4.48 (t, J=5.5 Hz, 2H), 3.22 (m, 2H), 2.99 (t, J=5.0 Hz, 2H), 2.56 (s, 6H), 1.66 (pent, J=7.4 Hz, 2H), 1.45 (sext, J=7.4 Hz, 2H), 0.97 (t, J=7.4 Hz, 3H). $^{13}$C NMR (125 MHz) ($CDCl_3$) δ: 165.6, 147.9, 130.7, 130.3, 118.1, 117.9, 109.5, 60.9, 57.1, 44.8, 43.0, 31.1, 20.2, 13.8. ESI-MH$^+$: calculated, 299.82; observed, 299.15.

4-(octylamino)-3-nitrobenzoic acid (Compound 13a)

Prepared as described for 11a using 3a and N-octylamine to yield 13a (30%).

4-(octylamino)-3-methoxybenzoic acid (Compound 13b)

Prepared as described for 11b using 4b and octanal to yield 13b (84%).

4-(octylamino)-3-methylbenzoic acid (Compound 13c)

Prepared as described for 11b using 4c and octanal to yield 13c (50%).

4-(octylamino)-3-fluorobenzoic acid (Compound 13e)

Prepared as described for 11b using 4-amino-3-fluorobenzoic acid (4e) and octanal to yield 13e (95%).

4-(octylamino)-3-bromobenzoic acid (Compound 13f)

Prepared as described for 11b using 4-amino-3-bromobenzoic acid (4f) and octanal to yield 13f (93%).

4-(octylamino)-2-chlorobenzoic acid (Compound 13g)

Prepared as described for 11b using 4-amino-2-chlorobenzoic acid (4g) and octanal to yield 13g (78%).

2-(dimethylamino)ethyl 4-(octylamino)-3-nitrobenzoate (Compound 14a)

Prepared as described for 12a using 13a to yield 14a (85%) as a yellow powder. $^1$H NMR (500 MHz) ($CDCl_3$) δ: 8.87 (d, J=2.1 Hz, 1H), 8.36 (br, 1H), 8.06 (dd, J=9.1, 2.1 Hz, 1H), 6.86 (d, J=9.1 Hz, 1H), 4.45 (t, J=5.8 Hz, 2H), 3.35 (m, 2H), 2.82 (t, J=5.5 Hz, 2H), 2.43 (s, 6H), 1.74 (pent, J=7.4 Hz, 2H), 1.2-1.5 (m, 10H), 0.88 (t, J=7.2 Hz, 3H). $^{13}$C NMR (125 MHz) ($CDCl_3$) δ: 165.1, 147.9, 136.4, 131.1, 129.7, 116.7, 113.6, 62.3, 57.5, 45.4, 43.3, 31.8, 29.7, 29.2, 29.14, 26.9, 22.6, 14.09. ESI-MH$^+$: calculated, 366.47; observed, 366.24.

2-(dimethylamino)ethyl 4-(octylamino)-3-methoxybenzoate (Compound 14b)

Prepared as described for 12a using 13b to yield 14b (18%) as light brown powder. $^1$H NMR (500 MHz) ($CDCl_3$) δ: 7.63 (dd, J=8.3, 1.8 Hz, 1H), 7.39 (d, J=1.8 Hz, 1H), 6.51 (d, J=8.4 Hz, 1H), 4.68 (t, J=5.4 Hz, 1H), 4.42 (t, J=5.8 Hz, 1H), 3.88 (s, 3H), 3.17 (m, 2H), 2.80 (t, J=5.6 Hz, 2H), 2.41 (s, 6H), 1.64 (pent, J=7.4 Hz, 2H), 1.2-1.45 (m, 10H), 0.88 (t, J=7.1 Hz, 3H). $^{13}C$ NMR (125 MHz) ($CDCl_3$) δ: 167.0, 145.5, 142.7, 124.8, 116.6, 109.8, 107.6, 61.9, 57.8, 55.6, 45.6, 43.1, 31.8, 29.7, 29.4, 29.3, 27.1, 22.7, 14.1. ESI-$MH^+$: calculated, 351.50; observed, 351.1.

2-(dimethylamino)ethyl 4-(octylamino)-3-methylbenzoate (Compound 14c)

Prepared as described for 12a using 13c to yield 14c (24%) as light brown powder. $^1H$ NMR (500 MHz) ($CDCl_3$) δ: 7.82 (dd, J=8.6, 2.0 Hz, 1H), 7.72 (m, 1H), 6.54 (d, J=8.6 Hz, 1H), 4.40 (t, J=5.8 Hz, 1H), 3.19 (t, J=7.2 Hz, 2H), 2.78 (t, J=5.8 Hz, 2H), 2.38 (s, 6H), 2.13 (s, 3H), 1.66 (pent, J=7.4 Hz, 2H), 1.2-1.45 (m, 10H), 0.88 (t, J=7.1 Hz, 3H). $^{13}C$ NMR (125 MHz) ($CDCl_3$) δ: 175.6, 167.0, 150.3, 131.6, 129.9, 120.5, 117.2, 108.2, 61.6, 57.5, 45.3, 43.5, 31.8, 29.4, 29.3, 27.1, 22.7, 17.2, 14.1. ESI-$MH^+$: calculated, 335.27; observed, 335.50.

2-(dimethylamino)ethyl 4-(octylamino)-3-chlorobenzoate (Compound 14d)

Prepared as described for 12d using 2 to yield 14d (71%) as oily, brown crystals. $^1H$ NMR (500 MHz) ($CDCl_3$) δ: 7.93 (d, J=2.0 Hz, 1H) 7.83 (dd, J=8.6, 2.0 Hz, 1H), 6.60 (d, J=8.6 Hz, 1H), 4.74 (br, 1H), 4.39 (t, J=5.8 Hz, 2H), 3.21 (m, 2H), 2.74 (m, 2H), 2.37 (s, 6H), 1.68 (m, 2H), 1.25-1.43 (m, 10H), 0.88 (t, J=7.1 Hz, 3H). $^{13}C$ NMR (125 MHz) ($CDCl_3$) δ: 166.3, 148.0, 131.1, 130.5, 118.3, 109.9, 108.68, 58.2, 46.0, 43.7, 32.1, 30.0, 29.7, 29.6, 29.4, 27.4, 23.0, 14.5. ESI-$MH^+$: calculated, 355.50; observed, 355.92.

2-(dimethylamino)ethyl 4-(octylamino)-3-fluorobenzoate (Compound 14e)

Prepared as described for 12a using 13e to yield 14e (75%) as white powder. $^1H$ NMR (500 MHz) ($CDCl_3$) δ: 7.72 (dd, $J_{HH}$=8.5, 1.8 Hz, 1H), 7.60 (dd, $J_{FH}$=12.5, $J_{HH}$=1.9 Hz, 1H), 6.60 (dd, $J_{FH}$=8.5, $J_{HH}$=8.5 Hz, 1H), 4.35 (t, J=5.9 Hz, 2H), 4.30 (br, 1H), 3.17 (m, 2H), 2.67 (t, J=5.9 Hz, 2H), 2.31 (s, 6H), 1.63 (m, 2H), 1.23-1.40 (m, 10H), 0.87 (t, J=7.0 Hz, 3H). $^{13}C$ NMR (125 MHz) ($CDCl_3$) δ: 166.5 (d, $^1J_{CF}$=2.7 Hz), 150.4 (d, $^4J_{CF}$=239 Hz), 141.40 (d, $^2J_{CF}$=11.4 Hz), 127.8 (d, $^4J_{CF}$=2.5 Hz), 117.7 (d, $^3J_{CF}$=6.5 Hz), 115.7 (d, $^2J_{CF}$=19.9 Hz), 110.4 (d, $^3J_{CF}$=3.6 Hz), 63.0, 58.3, 46.2, 43.4, 32.1, 29.7, 29.6, 27.4, 23.0, 14.4. ESI-$MH^+$: calculated, 339.47; observed, 339.17.

2-(dimethylamino)ethyl 4-(octylamino)-3-bromobenzoate (Compound 14f)

Prepared as described for 12a using 13f to yield 14f (70%) as oily, light brown crystals. $^1H$ NMR (500 MHz) ($CDCl_3$) δ: 8.11 (d, J=2.0 Hz, 1H), 7.87 (dd, J=8.5, 1.8 Hz, 1H), 6.58 (d, J=8.7 Hz, 1H), 4.77 (br, 1H), 4.38 (t, J=5.9 Hz, 2H), 3.21 (m, 2H), 2.70 (t, J=5.9 Hz, 2H), 2.34 (s, 6H), 1.69 (m, 2H), 1.26-1.44 (m, 10H), 0.90 (t, J=7.0 Hz, 3H). $^{13}C$ NMR (125 MHz) ($CDCl_3$) δ: 166.2, 148.9, 134.4, 131.1, 119.0, 109.9, 108.7, 63.0, 58.23, 46.2, 43.9, 32.1, 29.6, 29.5, 29.4, 27.4, 23.0, 14.5. ESI-$MH^+$: calculated, 399.7, 401.7; observed, 399.09, 401.12.

2-(dimethylamino)ethyl 4-(octylamino)-2-chlorobenzoate (Compound 14g)

Prepared as described for 12a using 13g to yield 14g (45%) as a light yellow powder. $^1H$ NMR (500 MHz) ($CDCl_3$) δ: 7.80 (d, J=8.7 Hz, 1H), 6.57 (d, J=2.4 Hz, 1H), 6.42 (dd, J=8.7, 2.4 Hz, 1H), 4.37 (t, J=6.0 Hz, 2H), 4.10 (br, 1H), 3.12 (m, 2H), 2.70 (t, J=6.0 Hz, 2H), 2.33 (s, 6H), 1.62 (m, 2H), 1.28-1.40 (m, 10H), 0.89 (t, J=7.0 Hz, 3H). $^{13}C$ NMR (125 MHz) ($CDCl_3$) δ: 165.6, 152.2, 136.9, 134.1, 116.5, 114.0, 110.5, 62.9, 58.2, 46.2, 43.7, 32.1, 29.6, 29.6, 29.5, 27.4, 23.0, 14.4. ESI-$MH^+$: calculated, 355.92; observed, 355.13.

Example 10

Compound 8 and Compound 9 are Effective in a Mouse Model of Retinal Degeneration The rd1 mouse is a newer designation for the classic rd mouse, which harbors a nonsense mutation in the PDE6B gene. The rd10 mouse contains a missense mutation in the same gene and leads to slower degeneration (Chang B et al, Vision Res 42, 517-525 (2002) and Gargini C et al, J Comp Neurol 500, 222-238 (2007), both of which are incorporated by reference herein.) There are advantages to each mutant for evaluating protection strategies. The rd phenotype has been studied for many years, and allows for more rapid assessment of protection strategies. However, the onset of rod photoreceptor death overlaps with the later stages of development and synaptogenesis, making it difficult to distinguish between the primary effects of rod degeneration and the consequences of abnormal neural development. The rd10 phenotype is more reminiscent of typical human RP.

Figure 8:
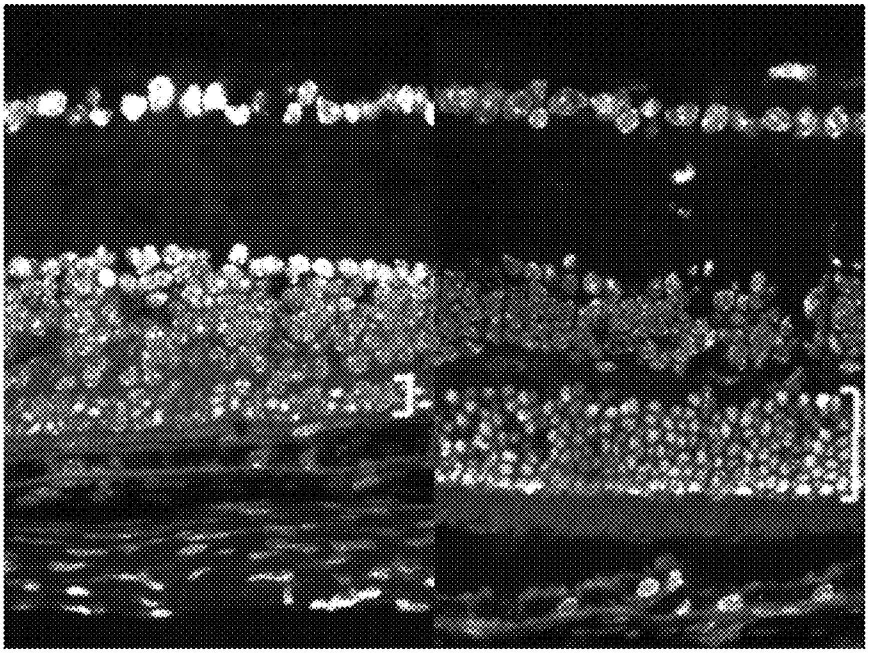
FIG. 8 is a set of two images of retinal sections from the left eye (left panel) and right eye (right panel) of an rd10 mouse, intravitreally injected with PBS and 5 mM compound 9 (final concentration ~0.5 mM), respectively, at P15 and euthanized at P25. Retinas were sectioned at 20 microns, and stained with DAPI. Images are confocal stacks taken very close to the optic nerve. The outer nuclear layers corresponding to photoreceptor cells are shown with white brackets.

FIG. 8 shows an experiment on rd10 mice in which striking neuroprotection of the photoreceptor layer was observed with intravitreal injection of a high concentration of compound 9 in the right eye (final concentration ~0.5 mM), while the left eye was injected with PBS and showed the typical degeneration observed at P25. In separate experiments on adult wild-type mice, the ERG a and b waves were blocked during a similar 10-day treatment, as expected for a concentration in excess of that required to completely block CNG channels. In the rd10 mouse some degeneration was probably underway before the treatment began.

Figure 9:
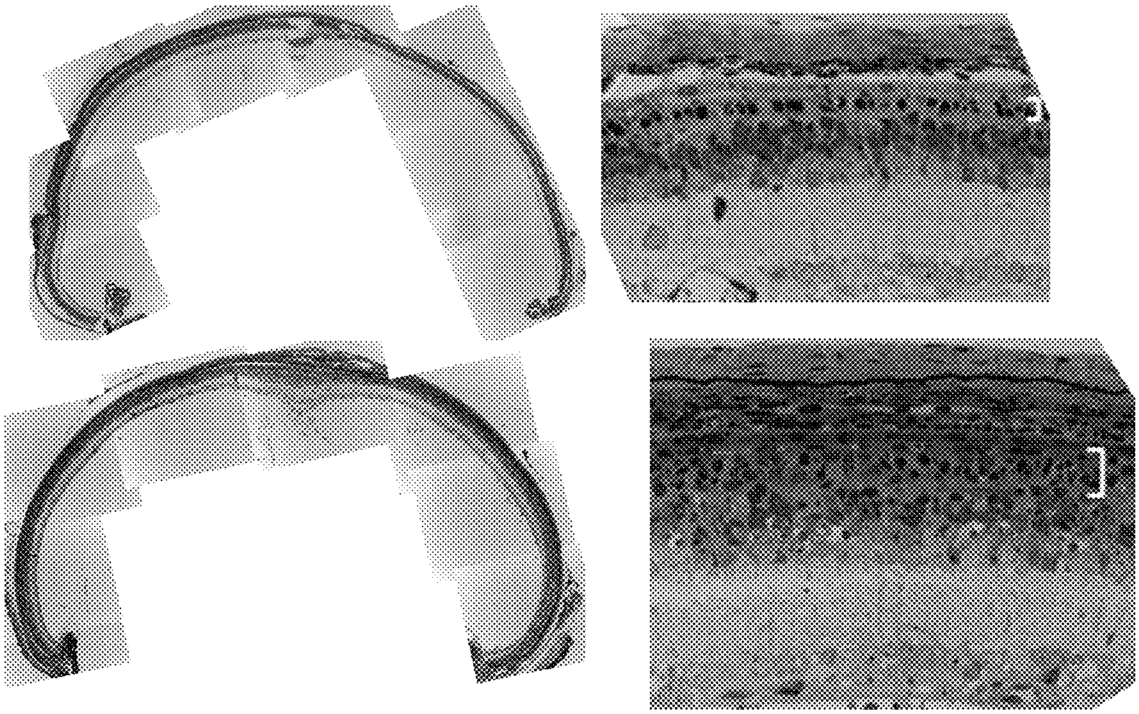
FIG. 9 is a set of four images of retinal sections from an untreated rd1 mouse euthanized at P17 (upper panels) and an rd1 mouse receiving a subretinal injection of 30 μM compound 8 (final concentration ~5 μM) at P12 and euthanized at P17 (lower panels). The photographs show standard histological analysis of retinal sections stained with cresol purple. The right panels are expansions of similar regions in each retina near the optic nerve. The white brackets mark the outer nuclear layer containing photoreceptor nuclei.

FIG. 9 is a comparison of two rd1 eyes, one untreated (upper panel) and one receiving a subretinal injection of compound 8 to an estimated final concentration of 5 μM at P12. Both eyes were harvested at P17 and there is a very noticeable rescuing effect of compound 8. The outer nuclear layer was only one cell thick in the untreated eye, and about three cells thick in the treated eye. Indeed, the entire retina was healthier in appearance in the treated eye.

What is claimed is:

1. A compound with the structure:

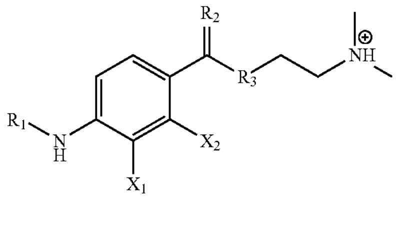

wherein $R_1$ is alkyl, $R_2$ is S, $R_3$ is O or NH, $X_1$ is H, nitro, methoxy, methyl, cyano or halo, and $X_2$ is H, nitro, methoxy, methyl, cyano or halo.

2. The compound of claim 1 with the structure:

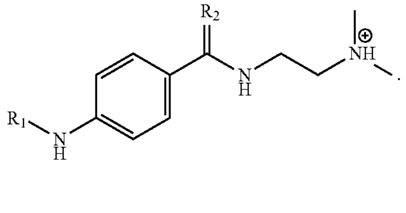

3. The compound of claim 2 wherein $R_1$ is selected from butyl or octyl.

4. The compound of claim 1 with the structure:

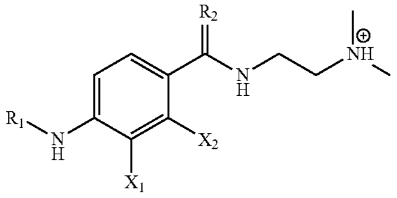

wherein $X_1$ is H or halo; and wherein $X_2$ is H or halo.

5. The compound of claim 4 wherein $R_1$ is octyl.

6. The compound of claim 5 wherein $X_1$ is H and $X_2$ is halo.

7. The compound of claim 5 wherein $X_1$ is halo and $X_2$ is H.

8. A pharmaceutical composition comprising an effective amount of the compound of claim 1 and a pharmaceutically acceptable carrier.

* * * * *

UNITED STATES PATENT AND TRADEMARK OFFICE

CERTIFICATE OF CORRECTION

PATENT NO. : 9,458,102 B2
APPLICATION NO. : 13/715334
DATED : October 4, 2016
INVENTOR(S) : Jeffrey Karpen et al.

It is certified that error appears in the above-identified patent and that said Letters Patent is hereby corrected as shown below:

In the Specification

At Column 1, Lines 12-16, under the heading ACKNOWLEDGEMENT OF GOVERNMENT SUPPORT, please delete the following:
"This invention was made with the support of the United States government under grant numbers R01 EY009275 and R01 MH071625, both of which were awarded by the National Institutes of Health."

And replace it with the following:
-- This invention was made with government support under EY009275 and MH071625 awarded by the National Institutes of Health. The government has certain rights in the invention. --

Signed and Sealed this
Sixteenth Day of July, 2019

Andrei Iancu
*Director of the United States Patent and Trademark Office*